US008162958B2

(12) United States Patent
Takahashi et al.

(10) Patent No.: US 8,162,958 B2
(45) Date of Patent: Apr. 24, 2012

(54) TISSUE FASTENING TOOL AND APPLICATOR FOR INDWELLING THE SAME WITHIN BODY, AND TISSUE FASTENING METHOD THROUGH NATURAL ORIFICE

(75) Inventors: Shinji Takahashi, Tokyo (JP);
Masatoshi Sato, Yokohama (JP);
Kazushi Murakami, Tokyo (JP);
Tetsuya Yamamoto, Hannou (JP)

(73) Assignee: Olympus Medical Systems Corp., Tokyo (JP)

( * ) Notice: Subject to any disclaimer, the term of this patent is extended or adjusted under 35 U.S.C. 154(b) by 717 days.

(21) Appl. No.: 12/171,817

(22) Filed: Jul. 11, 2008

(65) Prior Publication Data
US 2010/0010508 A1  Jan. 14, 2010

(51) Int. Cl.
*A61B 17/10* (2006.01)
(52) U.S. Cl. .................. 606/139; 606/142
(58) Field of Classification Search .............. 606/213, 606/215, 22, 223, 232, 198, 200, 151, 142, 606/139; 623/1.15, 1.22
See application file for complete search history.

(56) References Cited

U.S. PATENT DOCUMENTS

| 5,536,274 | A | | 7/1996 | Neuss |
| 5,582,616 | A | * | 12/1996 | Bolduc et al. .................. 606/143 |
| 5,830,221 | A | * | 11/1998 | Stein et al. .................... 606/157 |
| 6,113,611 | A | * | 9/2000 | Allen et al. .................... 606/151 |
| 6,117,157 | A | | 9/2000 | Tekulve |
| 6,551,340 | B1 | | 4/2003 | Kónya et al. |
| 6,635,066 | B2 | | 10/2003 | Tanner et al. |
| 6,663,633 | B1 | * | 12/2003 | Pierson, III .................... 606/148 |
| 6,790,218 | B2 | | 9/2004 | Jayaraman |
| 6,837,893 | B2 | | 1/2005 | Miller |
| 6,986,784 | B1 | * | 1/2006 | Weiser et al. .................. 623/1.1 |
| 7,131,979 | B2 | * | 11/2006 | DiCarlo et al. ............... 606/144 |
| 7,637,946 | B2 | | 12/2009 | Solem et al. |
| 7,722,636 | B2 | | 5/2010 | Farnan |
| 2002/0013605 | A1 | | 1/2002 | Bolduc et al. |
| 2003/0014127 | A1 | | 1/2003 | Talja et al. |

(Continued)

FOREIGN PATENT DOCUMENTS

JP 2005-193044 A 7/2005

(Continued)

OTHER PUBLICATIONS

Partial European Search Report dated May 31, 2010.

(Continued)

*Primary Examiner* — Corrine M McDermott
*Assistant Examiner* — Dianne Dornbusch
(74) *Attorney, Agent, or Firm* — Scully, Scott, Murphy & Presser, P.C.

(57) ABSTRACT

A tissue fastening apparatus related to the present invention includes; a tissue fastening tool formed of a wire wound into a coil shape provided with a first tissue fixing section which is hooked onto a first biological tissue and a second tissue fixing section which is hooked onto a second biological tissue; a tubular puncturing tool which extends a tissue fastening tool and accommodates the stretched tissue fastening tool inside of the puncturing tool; a fastening tool pusher in which the distal end thereof is inserted into the puncturing tool and dispenses the tissue fastening tool inserted into the puncturing tool from a distal end of the puncturing tool when the fastening tool pusher advances; and a rotating mechanism to rotate the puncturing tool when the fastening tool pusher advances.

11 Claims, 23 Drawing Sheets

U.S. PATENT DOCUMENTS

| | | |
|---|---|---|
| 2004/0073237 A1 | 4/2004 | Leinsing |
| 2005/0143763 A1* | 6/2005 | Ortiz et al. .................. 606/153 |
| 2005/0267495 A1* | 12/2005 | Ginn et al. ................... 606/151 |
| 2007/0225737 A1* | 9/2007 | Messerly et al. ............. 606/151 |
| 2008/0004640 A1* | 1/2008 | Ellingwood ................. 606/151 |
| 2008/0015633 A1* | 1/2008 | Abbott et al. ................ 606/207 |
| 2008/0208214 A1* | 8/2008 | Sato et al. .................... 606/139 |
| 2009/0069822 A1* | 3/2009 | Takahashi et al. ........... 606/139 |
| 2010/0010520 A1 | 1/2010 | Takahashi et al. |

FOREIGN PATENT DOCUMENTS

| | | |
|---|---|---|
| WO | WO 97/27898 A1 | 8/1997 |
| WO | WO 97/32527 | 9/1997 |
| WO | WO 02/19923 A1 | 3/2002 |
| WO | WO 03/105703 A2 | 12/2003 |
| WO | WO 2004/026113 A2 | 4/2004 |

OTHER PUBLICATIONS

Partial European Search Report dated May 3, 2010.

U.S. Office Action dated Jun. 16, 2011, in related U.S. Appl. No. 12/171,816.

U.S. Office Action dated Jul. 27, 2011, in related U.S. Appl. No. 12/430,442.

U.S. Office Action dated Jul. 27, 2011, in related U.S. Appl. No. 12/430,484.

U.S. Official Action mailed Dec. 15, 2011 in related U.S. Appl. No. 12/430,442.

* cited by examiner

TISSUE FASTENING TOOL AND APPLICATOR FOR INDWELLING THE SAME WITHIN BODY, AND TISSUE FASTENING METHOD THROUGH NATURAL ORIFICE

BACKGROUND OF THE INVENTION

1. Field of the Invention

The present invention relates to an applicator and tissue fastening method to perform a procedure for fastening tissues through a natural orifice.

2. Description of Related Art

Laparoscopic surgery which is transcutaneous insertion of medical instruments as a treatment of body organs is well known. This method is less invasive compared to incising the abdomen, and quick recovery is anticipated.

A medical instrument used for laparoscopic surgery has a shaft made of hard material inserted in the body transcutaneously, with forceps and so on provided at the front end of the shaft. For example, a treatment instrument used in applications such as connecting hollow organs is disclosed in Japanese Unexamined Patent Application, First Publication No. 2005-193044. This intraluminal anastomosis device has a grasper that can freely open and close fitted to the front end of the shaft, and a fastening tool inserted in the shaft.

The fastening tool can be pushed out from the front end of the shaft by the protruding device located proximally with respect to the operator. The fastening tool is formed by annealing (or heat treating) shape memory alloy into a flat coil shape and inserting it in the shaft in the elongated condition. When the fastening tool is used, the clamp is pushed out from the protruding device and inserted into the body. The fastening tool is heated by body temperature and restored to its original coil shape. The hollow organs are joined by the restored fastening tool.

Other examples of dispensing the fastening tool are disclosed in the international publication number WO2002/019923. Here, the fastening tool is pushed out from the needle and dispensed to the tissue. For this reason, an anchor is provided to control the depth to which the needle pierces the tissue and the amount of the fastening tool dispensed into the tissue. When performing the procedure, the instrument containing the fastening tool and the needle is punctured to the tissue. The needle is advanced to pierce the layers of tissue, and the position of the fastening tool is fixed by the anchor. Thereafter, the needle is pulled out from the tissue. The fastening tool does not move because of the anchor; therefore, its front end part remains inside of the inside layer of tissue. When the instrument is removed from the tissue, the rest of the fastening tool remains outside of the outside layer of tissue. When the fastening tool is restored into its original coil shape, the layers of the tissue are fastened.

SUMMARY OF THE INVENTION

The present invention relates to a tissue fastening tool formed of a wire wound into a coil-shape which fastens a first biological tissue and a second biological tissue provided with a first tissue fixing section which is hooked onto the first biological tissue and a second tissue fixing section which is hooked onto the second biological tissue, and at least a connecting portion between the first tissue fixing section and the second tissue fixing section is formed of a wire having a polygonal shaped cross section.

An applicator related to the present invention includes; a tubular puncturing tool which extends the tissue fastening tool formed of a wire wound into a coil-shape and the stretched tissue fastening tool being inserted thereinto; a fastening tool pusher in which the distal end thereof is inserted into the puncturing tool and dispense the tissue fastening tool inserted into the puncturing tool from a distal end of the puncturing tool when the fastening tool pusher advances; and a rotating mechanism to rotate the puncturing tool when the fastening tool pusher advances.

A tissue fastening apparatus related to the present invention includes; a tissue fastening tool formed of a wire wound into a coil-shape provided with a first tissue fixing section which is hooked onto a first biological tissue and a second tissue fixing section which is hooked onto a second biological tissue ; a tubular puncturing tool which extends the tissue fastening tool and accommodates the stretched tissue fastening tool therein; a fastening tool pusher in which the distal end thereof is inserted into the puncturing tool and dispenses the tissue fastening tool inserted into the puncturing tool from a distal end of the puncturing tool when the fastening tool pusher advances; and a rotating mechanism to rotate the puncturing tool when the fastening tool pusher advances.

A tissue fastening method of the present invention fastens a first biological tissue and a second biological tissue, where the method uses a tissue fastening tool formed of a wire wound into a coil-shape provided with a first tissue fixing section which is hooked onto the first biological tissue and a second tissue fixing section which is hooked onto the second biological tissue; the steps comprising: penetrating a tubular puncturing tool in which a stretched tissue fastening tool is accommodated into the first and the second biological tissues and dispensing the second tissue fixing section from the puncturing tool by rotating; extracting the puncturing tool from the first and the second biological tissues and dispending the first tissue fixing section from the distal end of the puncturing tool by rotating.

DETAILEDUODENUM DDESCRIPTION OF THE INVENTION

First Embodiment

Figure 1:
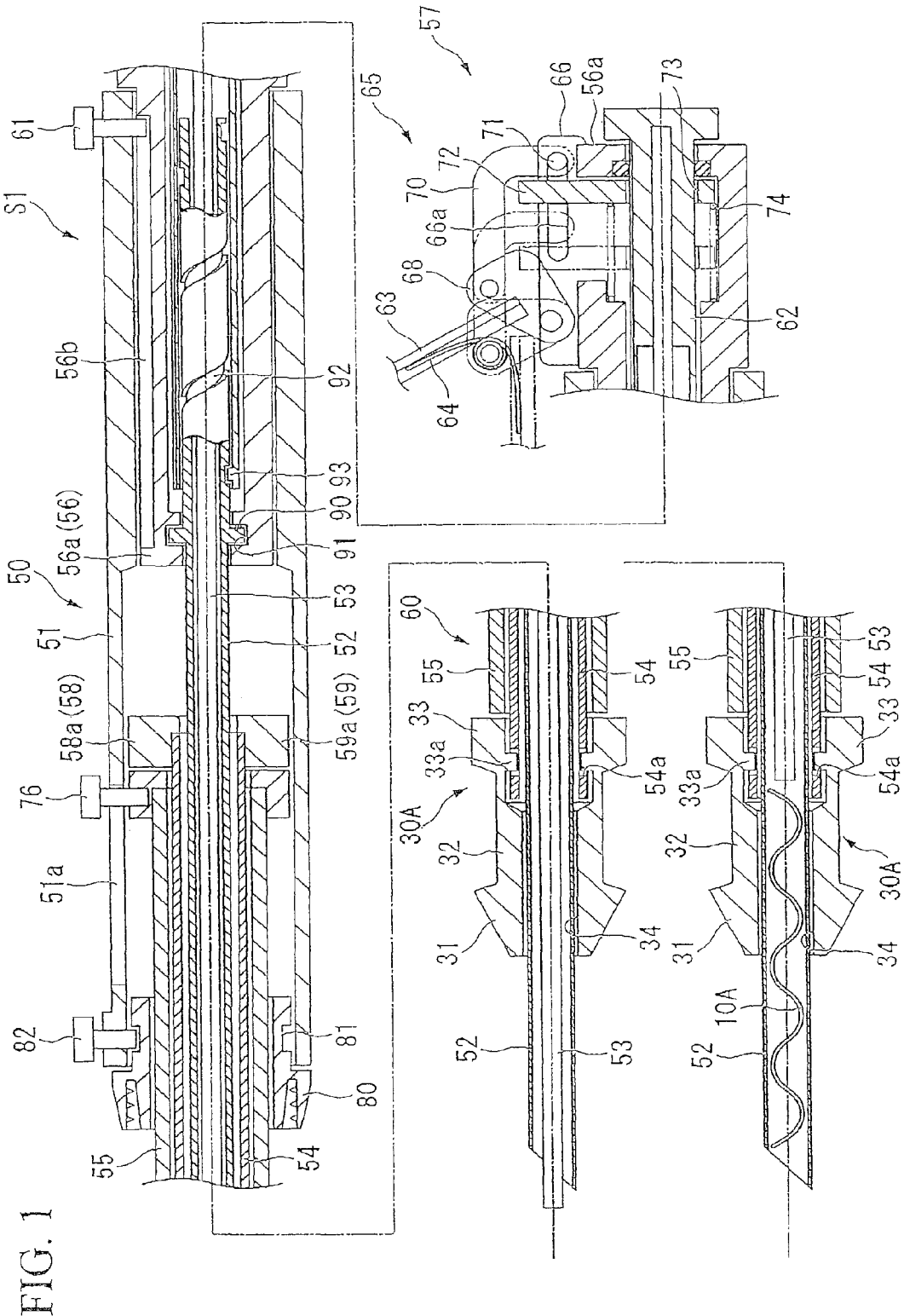
FIG. 1 shows the first embodiment of a tissue fastening apparatus of the present invention and is a cross-sectional view showing the internal structures of a tissue fastening tool, a stent and an applicator included in the apparatus.
Figure 2:
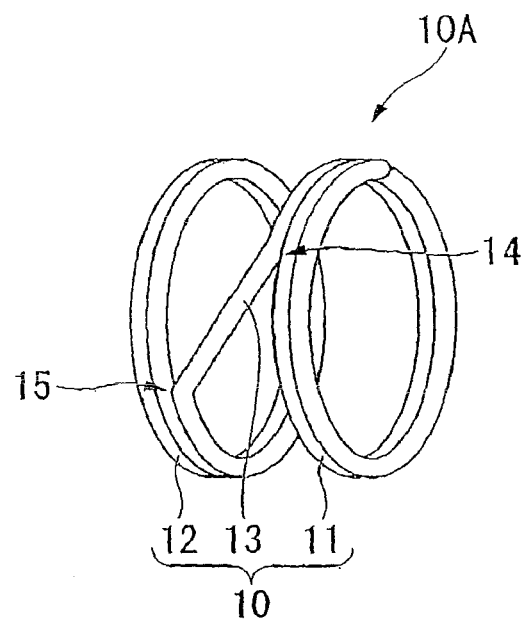
FIG. 2 is a perspective view showing the tissue fastening tool included in the tissue fastening apparatus.

A first embodiment according to the present invention will now be described here. As shown in FIG. 1, a tissue fastening apparatus S1 in the present embodiment is an apparatus which fixes a second biological tissue to a first biological tissue and communicate therethrough. The apparatus includes a tissue fastening tool 10A, a stent 30A and an applicator 50. Note that the first and second biological tissues are not limited to different organs; for example, a section of an organ may be referred to as the first biological tissue and a different section of the same organ may be referred to as the second biological tissue, so as to include fixing different sections within the same organ. In the present embodiment, a procedure to make a bypass between the duodenum as the first biological tissue and the common bile duct as the second biological tissue after fixing the second biological tissue to the first biological tissue is described here.

A tissue fastening tool 10A is a tool which fastens the duodenum and the common bile duct and is provided with a first tissue fixing section 11 which is hooked onto the duodenum and a second tissue fixing section 12 which is hooked onto the common bile duct adjacent to the duodenum. The tissue fastening tool 10A is further provided with the connector 13 connecting the first tissue fixing section 11 and the second tissue fixing section 12 therebetween.

Figure 3:
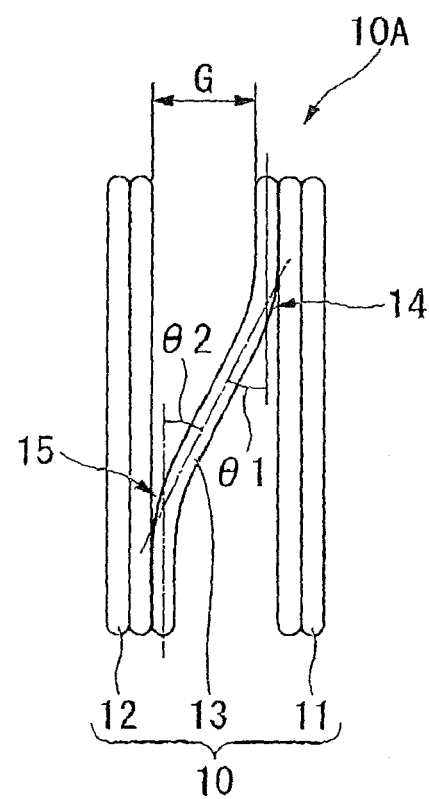
FIG. 3 is a plan view of the tissue fastening tool as seen from a different direction from the FIG. 2.

The tissue fastening tool 10A is formed of a super elastic element wire 10 wound into a coil shape for all sections, such as the first tissue fixing section 11, the second tissue fixing section 12 and the connector 13. Bending sections 14 and 15 are formed in the wire disposed between the first tissue fixing section 11 and the connector 13; and between the wire disposed between the connector 13 and the second tissue fixing section 12, respectively. Both the first tissue fixing section 11 and the second tissue fixing section 12 are formed into a coil shape with equal diameter and a gap G is created therebetween upon forming the connector 13. The central axis of the coil shaped first tissue fixing section 11 is corresponds to that of the coil shaped second tissue fixing section 12. As shown in FIG. 3, the wire forming the connector 13 forms an angle θ1 with the wire forming the coil shaped first tissue fixing section 11 at the bending section 14. The wire forming the connector 13 also forms an angle θ2 with the wire forming the coil shaped second tissue fixing section 12 at the bending section 15. The size of the angle θ1 formed at the bending section 14 is substantially the same as that of the angle θ2 formed at the bending section 15.

The tissue fastening tool 10A is stretched, and one end thereof is pierced into a biological tissue; the other end of the tissue fixing section, for example, the second tissue fixing section 12, is then penetrated through sequentially a wall of duodenum and a wall of common bile duct. The second tissue fixing section 12 penetrated through the wall of the duodenum and the wall of the common bile duct is restored to its original coil shape at the inside of the common bile duct since a tension exerted on the wire is released, and is hooked onto the common bile duct. On the other hand, the first tissue fixing section 11 is hooked onto the duodenum by restoring to its original coil shape at inside of the duodenum since a tension exerted on the wire is released. The wall of the duodenum and the wall of the common bile duct are fastened such that both walls are pressed against each other, by the first tissue fixing section 11 hooked onto the duodenum and the second tissue fixing section 12 hooked onto the common bile duct. The connector 13 is placed within both walls of the organs.

As shown in FIG. 1, the stent 30A is a tool which penetrates through the wall of the duodenum and the wall of common bile duct fastened by the tissue fastening tool 10A, and is provided with a dilating portion 31, an indwelled portion 32, a fall-off prevention portion 33 and a through hole 34. The dilating portion 31 forms a conical shape in which the diameter increases from a front end to substantially a rear end. The indwelled portion 32 forms a conical shape disposed behind of the dilating portion 31. A diameter of the indwelled portion 32 is uniform and is smaller than the maximum outer diameter of the dilating portion 31. The fall-off prevention portion 33 forms a cylindrical shape and is disposed behind of the indwelled portion 32. An outer diameter of the fall-off prevention portion 33 is larger than that of the indwelled portion 32. The through hole 34 passes through the dilating portion 31, the indwelled portion 32 and the fall-off prevention portion 33 in a horizontal direction of the stent 30A.

A plurality of projections 33a which are formed in a radial direction of the stent 30A is disposed on an inner face of the fall-off prevention portion 33. The projections 33a are comprised of a part of a mounting section in which the stent 30A is detachably disposed on the sheath 54 of the applicator 50 which will be described later.

As for the materials used to make the stent 30A may be selected from any one of or a polymer of; stainless steel (SUS), titanium (Ti), bioabsorbable magnesium, polyethylene (PE), polyetheretherketone (PEEK), polysulfone, liquid crystal polymer, polylactic acid, polyglycolic acid, polydioxanone, polyhydroxyalkanoates, and caprolactone. These materials have superb biocompatibilities to living tissues, hence there is little burden on a body while the stent 30A is placed in the body. In particular, polylactic acid, polyglycolic acid, polydioxanone, polyhydroxyalkanoates and caprolactone degrade over a period of time while they are placed in the body, and are consequently absorbed into the body. Therefore they are preferably selected since there are no foreign substances will remain in the body.

An applicator 50 is a tool to place the tissue fastening tool 10A and the stent 30A in the body, and is provided with an applicator main body 51, a puncturing tool 52, a stylet (fastening tool pusher) 53, a sheath 54 and a stent pusher 55 as shown in FIG. 1. The applicator main body 51 is in a tubular shape. The puncturing tool 52 is in a needle-like tubular shape accommodating the tissue fastening tool 10A therein with a state of the tissue fastening tool 10A being stretched. In addition, an electrode may be provided at a distal end of the puncturing tool 52 and pierced into the wall of the duodenum and the wall of the common bile duct by cauterizing the biological tissues. In this case, the distal end of the puncturing tool 52 may not have to be sharp.

The stylet 53 forms an elongated shape and is inserted into the puncturing tool 52 so as to be freely advanced and retracted within the puncturing tool 52, and dispenses the tissue fastening tool 10A housed in the puncturing tool 52 out from the distal end of the puncturing tool 52.

The puncturing tool 52 is inserted into the sheath 54 so as to be freely advanced and retracted within the sheath 54, and operates a movement of the stent 30A which is detachably disposed at the distal end thereof relative to the puncturing tool 52.

The tubular stent pusher 55 accommodates the sheath 54 so as to be freely advanced and retracted, and separates the sheath 54 from the stent 30A disposed at the distal end of the sheath 54.

The applicator main body 51 includes a puncturing tool operating section 56, a stylet operating section 57, a sheath operating section 58 and a stent pusher operating section 59. The puncturing tool 52, the stylet 53 and the sheath 54 are flexible, and are disposed along the same axial line. They consist of an insertion section 60 which is inserted into an instrument channel of an inserting section of an endoscope, hence the insertion section 60 is longer than the instrument channel of the endoscope.

The distal end surface of the puncturing tool 52 is obliquely formed along the longitudinal direction, in order to form the incisive front end of the puncturing tool 52. A proximal end of the puncturing tool 52 is connected to the puncturing tool operating section 56 provided at a rear portion of the applicator main body 51.

The distal end of the stylet 53 is smooth, not incisive. The proximal end of the stylet 53 is connected to the stylet operating section 57 as described later provided inside of the puncturing tool operating section 56.

A distal end surface of the sheath 54 is formed evenly in a direction perpendicular to the longitudinal direction of the sheath 54. A plurality of small holes 54a are disposed at the distal end of the sheath 54 with the same number or more of the projections 33a of the stent 30A. The small holes 54a are disposed in a peripheral direction of the sheath 54 penetrating through the wall of the sheath 54. The small holes 54a consist of a part of the mounting section where the stent 30A is detachably disposed to the sheath 54. When the distal end of the sheath 54 is pushed into the through hole 34 of the stent 30A from the rear end, the projections 33a are engaged to the small holes 54a. Hence the stent 30A is attached to the distal end of the sheath 54. Due to its flexibility, when the sheath 54 is pulled toward its rear direction upon placing the stent 30A at a fixed position, the sheath 54 is elastically deformed so as to detach from the small holes 54a. From this mechanism, the stent 30A separates from the distal end of the sheath 54. When the stent 30A is made of elastic materials, both of the sheath 54 and a protruded section of the stent 30A are elastically deformed so that the stent 30 also separates from the distal end of the sheath 54.

Here, the small holes 54a may not be limited to always penetrating through the wall of the sheath 54, the small holes may be indentations formed on the outer surface of the sheath 54. Protrusions may be formed on the sheath 54 as well as forming small holes on the stent 30A to engage therebetween.

The proximal end of the sheath 54 is connected to the sheath operating section 58 disposed at a front portion of the applicator main body 51.

The front face of the stent pusher 55 is formed evenly in a direction perpendicular to the longitudinal direction of the stent pusher 55. The proximal end of the stent pusher 55 is connected to the stent pusher operating section 59 disposed at the front portion of the applicator main body 51. The puncturing tool operating section 56 includes a cylindrical-shaped first shaft 56a inserted from the rear end of the applicator main body 51 into the inner layer thereof. An outer diameter of the first shaft 56a is slightly smaller than an inner diameter of the rear portion of the applicator main body 51. Therefore, the first shaft 56a can be slid with respect to the inner layer of the rear portion of the applicator main body 51. The proximal end of the puncturing tool 52 is fixed to the distal end of the first shaft 56a inserted into the applicator main body 51 so as to align the longitudinal direction of the puncturing tool 52 with the longitudinal direction of the first shaft 56a. The puncturing tool 52 can change its position relative to the applicator main body 51 by making the first shaft 56a slide against the applicator main body 51.

An external thread hole is formed in a radial direction at the rear portion the applicator main body 51 and an external thread 61 is screwed thereinto. The distal end of the external thread 61 is projected into the applicator main body 51. On the other hand, a groove 56b is formed along the longitudinal direction of the first shaft 56a on the outer surface of the first shaft 56a. A distal end of the external thread 61 is loosely screwed into the groove 56b of the first shaft 56a inserted into the applicator main body 51. From the above structure, the groove 56b controls a range of movement of the first shaft 56a with respect to the applicator main body 51. The external thread 61 is further screwed into the external thread hole and the distal end of the external thread 61 is pressed against the bottom surface of the groove 56b so as to be able to hold the first shaft 56a with respect to the applicator main body 51 at any desired position.

The stylet operating section 57 includes a cylindrical-shaped second shaft 62 inserted from the rear end of the first shaft 56a thereinto, a lever 63 supported by the first shaft 56a which also supports the puncturing tool 52 so as to oscillate, a twisted coil spring 64 which spring-biases the lever 63 to the direction in which the lever 63 detaches from the applicator main body 51, and a linkage 65 which translates the oscillating movement of the lever 63 into a liner motion along the puncturing tool 52 of the stylet 53.

A proximal end of the stylet 53 is inserted from the distal end of the second shaft 62 into the inside thereof and is fixed so as to align the longitudinal direction of the stylet 53 with the longitudinal direction of the second shaft 62. The stylet 53 can change positions relative to the puncturing tool 52 by sliding the second shaft 62 with respect to the first shaft 56a.

A projection 90 is disposed on an outer periphery of the puncturing tool 52 and engages a ring groove 91 formed on an inner periphery of a distal end of the puncturing tool operating section 56. Thereby, the puncturing tool 52 is capable of rotating relative to the puncturing tool operating section 56. However, the movement into an axial direction is prevented. A spiral groove 92 is formed on an outer periphery of the puncturing tool 52 at a proximal side with respect to the projection 90. A pin-shaped projection 93 is provided on an inner periphery surface of a second shaft 62 opposing the outer periphery surface of the puncturing tool 52 so as to engage with the spiral groove 92. In addition, a longitudinal groove 94 is formed on an outer periphery of the second shaft 62. A projection 95 is formed on an inner periphery section of a plate member 72 and engages with the longitudinal groove 94. Thereby the second shaft 62 is capable of moving to an axial direction while the rotation relative to the plate member 72 is prevented. A function of rotating mechanism 96 to rotate the puncturing tool 52 is achieved when the second shaft 62 in which the rotation is prevented advances or retracts along the axial direction by the ring groove 91 and the projection 90, and the spiral groove 92 and the projection 93 which correspond to each other.

When the puncturing tool 52 rotates in conjunction with the movement of the second shaft 62 to the axial direction, the spiral shape of the spiral groove 92 is predetermined so that the rotating direction of the puncturing tool 52 and the direction of coil winding of the tissue fastening tool 10A are set to be opposite. Furthermore, as described above, every time the tissue fastening tool 10A is dispensed from the distal end of the puncturing tool 52 by one-coil winding with the movement of the second shaft 62 to the axial direction, a spiral shape of the spiral groove 92 is determined so that the puncturing tool 52 rotates one revolution. In this embodiment, the spiral groove 92 and the projection 93 are disposed on the outer periphery of the puncturing tool 52 and the inner periphery of the second shaft 62, respectively. However, the present invention is not limited thereto; in reverse, the projection and the spiral groove may be disposed on the outer periphery of the puncturing tool 52 and the inner periphery of the second shaft 62, respectively.

Figure 4A:
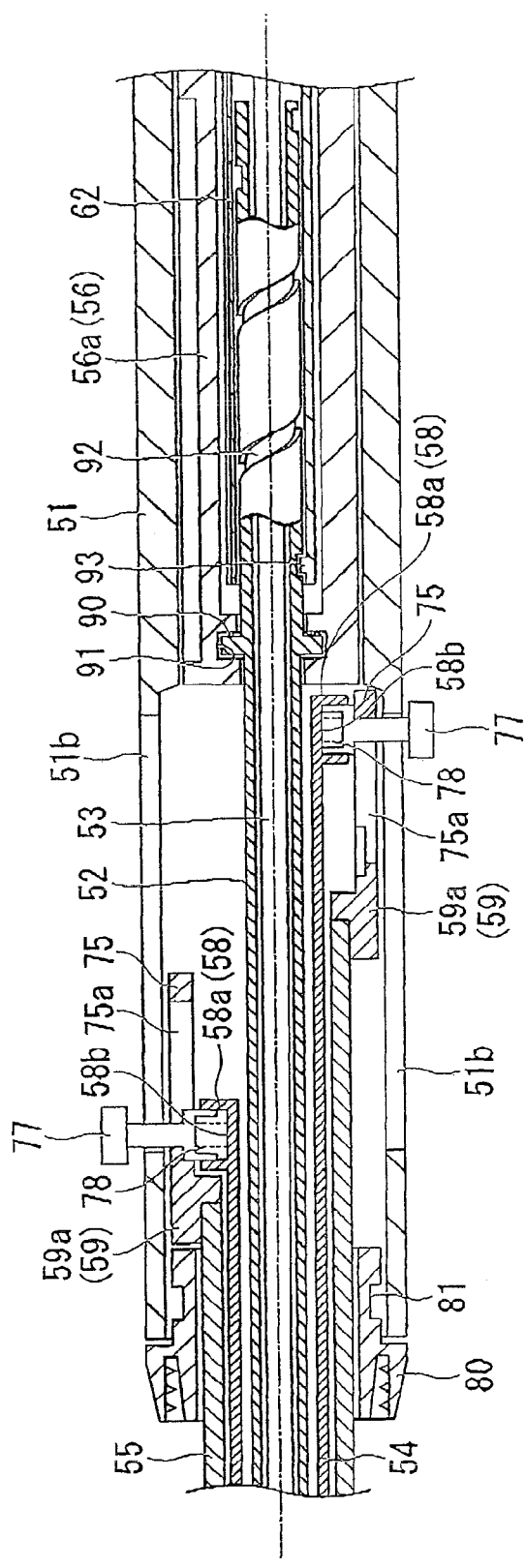
FIG. 4 shows a constitution of the first and the second ring members disposed in the applicator within the apparatus, the top half shows a state in which the first and the second ring members are moved to the front end of the applicator, and the bottom half shows a state in which the first and the second ring members are moved to the rear end of the applicator.
Figure 4B:
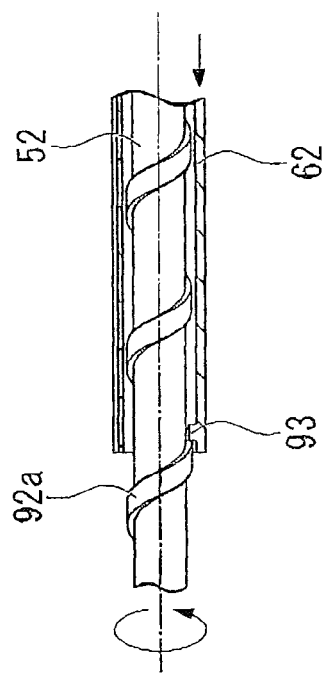

Furthermore, as shown in FIG. 4B, the spiral shape may consist of a convex shape rather than forming a groove. The same operation described hereinabove can be achieved by forming a spiral convex 92a on the outer periphery of the puncturing tool 52 and engaging the projection 93 formed on the inner periphery of the second shaft 62. Likewise, the same effect can also be achieved by forming the projection on the outer periphery of the puncturing tool 52 and engaging with the spiral convex formed on the inner periphery of the second shaft 62.

The linkage 65 includes a base 66, a bracket 68, a bar 70, a plate 72 and a compressed coil-spring 74. The base 66 is fixed on an outside of the first shaft 56a and the bracket 68 is strutted to the base 66 axially. A bottom end of the lever 63 is fixed to the bracket 68. The first end of the bar 70 is strutted to the bracket 68 axially and the second is strutted to the base 66 axially. A pin 71 which is provided at the second end of the bar 70 is loosely screwed into a long hole 66a formed along the sliding direction on the second shaft 62 of the base 66.

A hole 73 with a diameter that is larger than the outer diameter of the second shaft 62 is formed on the plate 72, and the second shaft 62 inserted into the first shaft 56a is penetrated through the hole 73.

A difference between the outer diameter of the second shaft 62 and the inner diameter of the hole 73 is extremely small, hence friction is exerted upon contacting the inner face of the hole 73 to the outer face of the second shaft 62 when the plate 72 is tilted and advanced in the longitudinal direction of the second shaft 62; in other words, toward the second shaft 62 inserted into the first shaft 56a. Therefore a force applied to the plate 72 is translated and exerted on the second shaft 62.

The compressed coil-spring 74 is disposed in the first shaft 56a, and biases the plate 72 to a direction opposite to the inserted direction of the second shaft 62 into the first shaft 56a.

When the lever 63 is moved toward the applicator main body 51, the bar 70 is pulled toward the front portion of the applicator main body 51 via the bracket 68 and the second end of the bar 70 is moved along the long hole 66a. The plate 72 is pushed by the second end of the bar 70, and is advanced to the inserted direction of the second shaft 62 into the first shaft 56a against spring-biases of the compressed coil-spring 74. At this time, the plate 72 is slightly tilted and friction occurs between the plate 72 and the second shaft 62, a force applied to the plate 72 is translated and exerted to the second shaft 62 so that the second shaft 62 is press-fitted into the first shaft 56a. When the lever 63 is released, the coil spring 64 detaches the lever 63 from the applicator main body 51; simultaneously the compressed coil-spring 74 pushes the plate 72 back to the original position without creating friction between the second shaft 62 and the plate 72.

Since the moving distance of the second end of the bar 70 per one operation on the lever 63 is always uniform, an insertion length of the second shaft 62 into the first shaft 56a per operation on the lever 63 is also uniform. Therefore it is possible to control the insertion length of the second shaft 62 into the first shaft 56a; in other words, an insertion amount of the stylet 53 into the puncturing tool 52 as per number of operations on the lever 63 can be controlled. This mechanism indicates that it is also possible to control the length of the tissue fastening tool 10A dispensed from the distal end of the puncturing tool 52 as per the number of operations on the lever 63.

Here, when the tissue fastening tool 10A forms into a coil shape as described in this embodiment, the insertion length of the stylet 53 per operation on the lever 63 is preferred to be substantially n or 1/n times (n is a positive integer) the circumference of the tissue fastening tool 10A. For example, if the insertion amount of the stylet 53 per operation on the lever 63 is substantially equal to the circumference of the tissue fastening tool 10A, the tissue fastening tool 10A is dispensed from the distal end of the puncturing tool 52 by one reel length every time the lever 63 is operated once. Furthermore, if the second tissue fixing section 12 consists of two reel lengths of the tissue fastening tool 10A, only the second tissue fixing section 12 can be dispensed from the distal end of the puncturing tool 52 by operating the lever 63 twice. Alternatively, if an insertion length of the stylet 53 per operation on the lever 63 is substantially equal to a half of the circumference of the tissue fastening tool 10A, the tissue fastening tool 10A is dispensed from the distal end of the puncturing tool 52 by a half reel length every time the lever 63 is operated once. Furthermore, if the second tissue fixing section 12 consists of two reel lengths of the tissue fastening tool 10A, only the second tissue fixing section 12 can be dispensed from the distal end of the puncturing tool 52 by operating the lever 63 four times.

A sheath operating section 58 is disposed inside of the applicator main body 51 and includes the first ring member 58a in which the puncturing tool 52 is inserted in the internal hole. An outer diameter of the first ring member 58a is slightly smaller than the internal diameter of the front portion of the applicator main body 51 and the internal diameter of the first ring member 58a is substantially equal to the internal diameter of the sheath 54. Therefore, the first ring member 58a can be slid with respect to the internal surface of the front portion of the applicator main body 51. The distal end of the sheath 54 is fixed to the front face of the first ring member 58a so as to align the center of the sheath 45 with that of the first ring member 58a. The position of the sheath 54 relative to the applicator main body 51 can be changed by sliding the first ring member 58a with respect to the applicator main body 51.

A stent pusher operating section 59 is disposed at, in particular, the front portion of the first ring member 58a in the applicator main body 51, and includes the second ring member 59a in which the sheath 54 is inserted into the internal hole. The outer diameter of the second ring member 59a is slightly smaller than the internal diameter of the front portion of the applicator main body 51, and the internal diameter of the second ring member 59a is substantially equal to the internal diameter of the tubular stent pusher 55. Thus the second ring member 59a is disposed in a slidable manner with respect to the internal diameter of the front portion of the applicator main body 51. The proximal end of the stent pusher 55 is fixed to a front face of the second ring member 59a so as to align the center of the stent pusher 55 with that of the second ring member 59a. The stent pusher 55 can change its position relative to the applicator main body 51 by sliding the second ring member 59a relative to the applicator main body 51.

As shown in FIG. 1 an external thread hole is formed on an outer side of the second ring member 59a in a radial direction of the second ring member 59a. On the other hand, a long hole 51a is formed at the front portion of the applicator main body 51 along the sliding direction of the second ring member 59a. An external thread 76 is screwed into the external thread hole on the second ring member 59a through the long hole 51a so that the long hole 51a can control an area of movement of the second ring member 59a with respect to the applicator main body 51. When the external thread 76 is further screwed into the external thread hole and the head portion of the thread abuts the applicator main body 51, the second ring member 59a can be maintained in its position with respect to the applicator main body 51.

Two concave shaped portions 58b are formed on the outer side of the first ring member 58a as shown in FIG. 4. On the other hand, two bars 75 projected to the rear side are disposed at the second ring member 59a. Long holes 75a are formed along the sliding direction of the first ring member 58a relative to the applicator main body 51 on each of the two bars 75. Further, two long holes 51b are also formed parallel to the long hole 75a on the applicator main body 51. Two pins 77 are inserted into each of the two concave portions 58b of the first ring member 58a by passing through the long holes 51b of the applicator main body 51 and the long hole 75a of the second ring member 59a so that the long hole 75a can control the area of movement of the first ring member 58a with respect to the second ring member 59a. Moreover, since the second ring member 59a slides relative to the applicator main body 51, the long holes 51b are designed to be formed so as to be longer than a length of the long hole 75a due to the area of movement of the second ring member 59a and the first ring member 58a.

Figure 5:
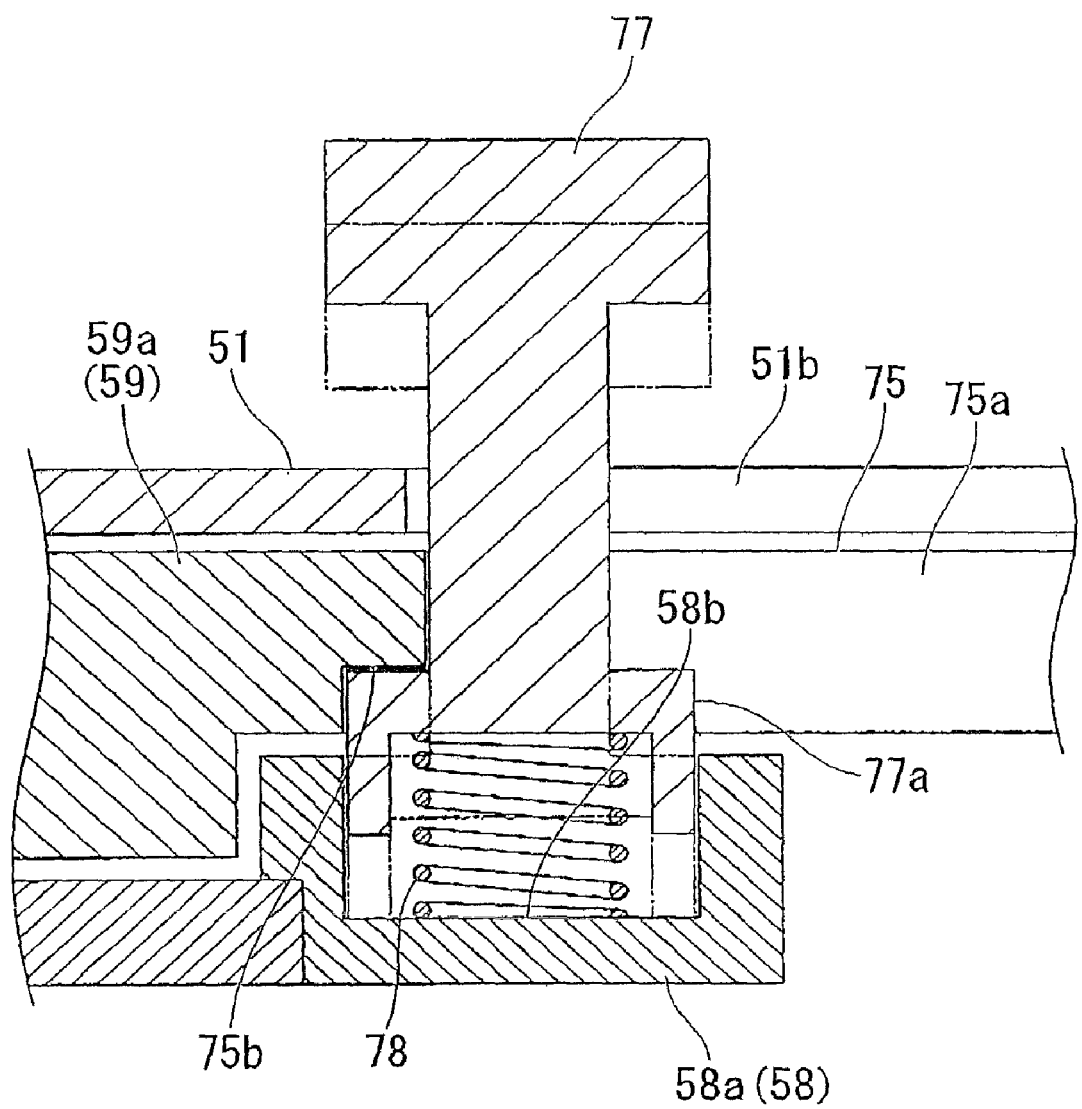
FIG. 5 is a cross-sectional view showing the structure of a pin to engage the first ring member onto the second ring member.

As shown in FIG. 5, a compressed spring 78 is disposed between the concave portion 58b and a distal end of the pin 77 so that the pin 77 is always biased toward the outside of the radial direction of the second ring member 59a. A concave portion 75b is formed on the bar 75 so as to fit with a large-diameter portion 77a of the pin 77 when the first ring member 58a is disposed in the vicinity of the front face of the second ring member 59a.

When the first ring member 58a is disposed in the vicinity of the front face of the second ring member 59a, the large-diameter portion 77a of the pin 77 engages with the concave portion 75b, hence the first ring member 58a is restrained by the second ring member 59a via the pin 77. When the pin 77 is press-fitted into the applicator main body 51 against the bias force of the compressed spring 78, the large-diameter portion 77a of the pin 77 is detached from the concave portion 75b, so that the first ring member 58a is released from the second ring member 59a so as to move toward the rear portion of the applicator main body 51. Therefore, it is possible to shift the sheath 54 to the proximal side with respect to the stent pusher 55.

A connector 80 is fitted to the distal end of the applicator main body 51. An inside screw is formed in the connector 80 so as to fix the applicator 50 on the endoscope 2 by screwing the inside screw into the connector 80 of the endoscope 2. A groove 81 is formed along a periphery direction on the outside of the connector 80. On the other hand, an external thread hole is formed on the applicator main body 51 in the radial direction and the external thread 82 is screwed into the external thread hole. A distal end of the external thread 82 is protruded inside of the applicator main body 51. The distal end of the external thread 82 is loosely screwed into the groove 81 of the connector 80 so as to freely rotate the applicator main body 51 relative to the connector 80 fixed to the endoscope 2. When the external thread 82 is further screwed into the external thread hole and the distal end of the screw 82 is abutted on a base of the groove 81, the applicator main body 51 can be held in its desirable position with respect to the connector 80.

Figure 6:
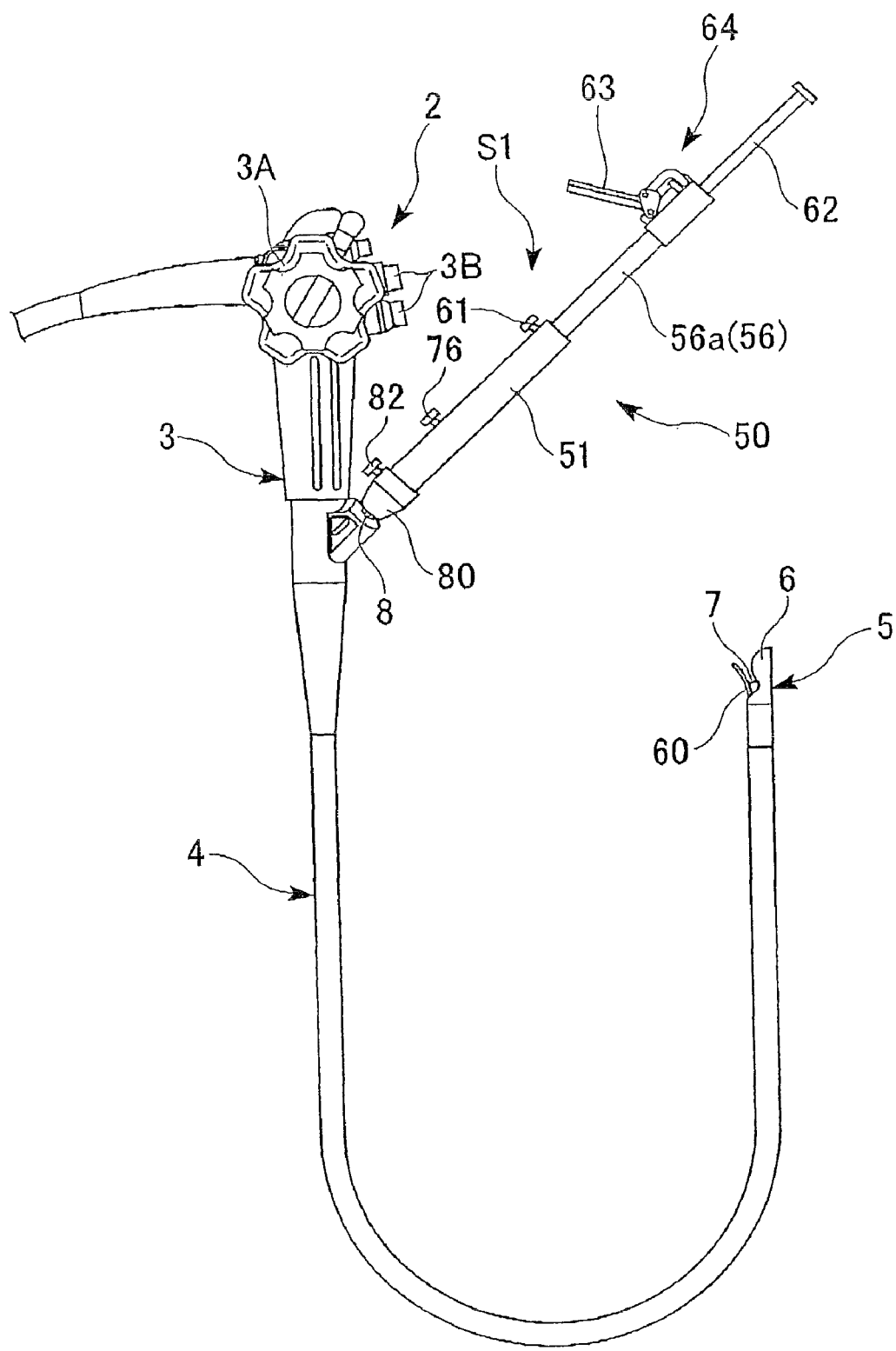
FIG. 6 shows a state in which an insertion section of the applicator is inserted into the instrument channel of the endoscope.

FIG. 6 shows the linear scanning type ultrasonic endoscope as the endoscope 2 used together with the tissue fasting apparatus S1. The endoscope 2 is provided with a flexible insertion portion 4 that extends from the operation part 3 used outside the body. A knob 3A for bending the front end part of the insertion portion 4 into a curved shape and various buttons 3B are provided in the operation part 3. A cover 5 is fitted at the front end of the insertion portion 4. An ultrasonic probe 6 is fitted to the cover 5. The ultrasonic probe 6 is placed on the flat plane passed through the axial line of the insertion portion 4. A plurality of ultrasonic transducers are disposed along the periphery of the circular arc shape. Furthermore, the endoscope 2 is provided with a forceps elevator 7 for delivery of the distal end portion of the applicator 50 in the lateral direction, and the direction of delivery of the applicator 50 can be adjusted at a portion located proximally with respect to the operator. The endoscope 2 may be provided with an ultrasonic probe of different types. Moreover, an endoscope not provided with the ultrasonic probe 6 may also be used. In this case, an ultrasonic probe used outside the body, an X-ray device, a magnetic resonance imaging (MRI) device, or a computerizing tomography (CT) device may be used jointly.

Figure 7:
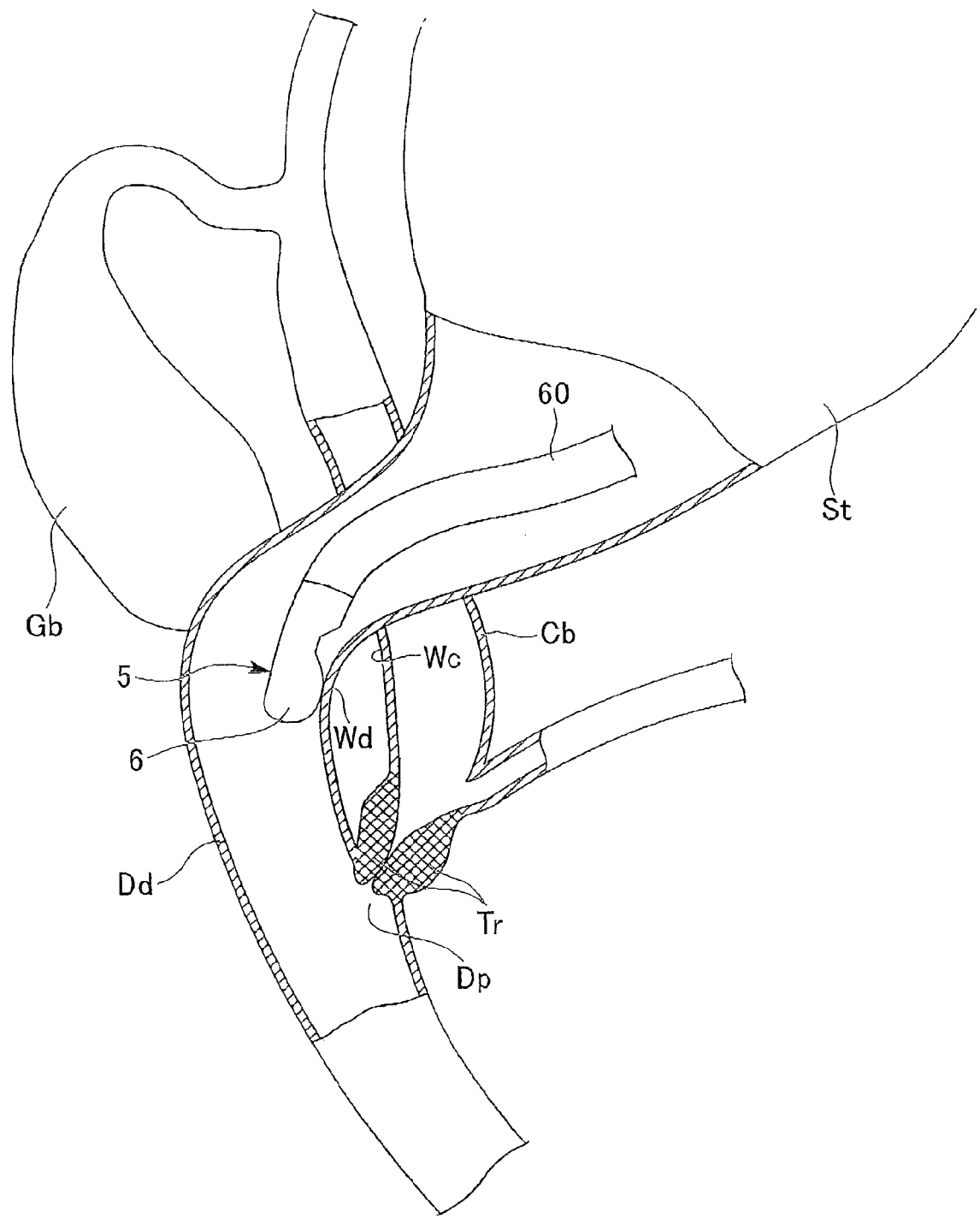
FIG. 7 shows a state in which the insertion section of the endoscope is inserted into the duodenum.

Next, the procedure to make a bypass between the common bile duct and the duodenum after joining them is described here. As shown in FIG. 7, this kind of procedure is performed when the duodenal papilla Dp is obstructed by a tumor Tr preventing bile drainage, consequently the bile assimilates in the blood causing jaundice. This procedure enables the direct drainage of bile from the common bile duct Cb to the duodenum Dd.

First, the insertion portion of the endoscope 2 is inserted from the patient's mouth. The endoscope 2 is inserted into the duodenum Dd, which is the upper alimentary tact. The condition outside the duodenum Dd is examined by the ultrasonic probe 6, and an appropriate location proximally with respect to the common bile duct Cb for the procedure is searched in the area vicinity to the stomach St side with respect to the duodenal papilla Dp.

Figure 8A:
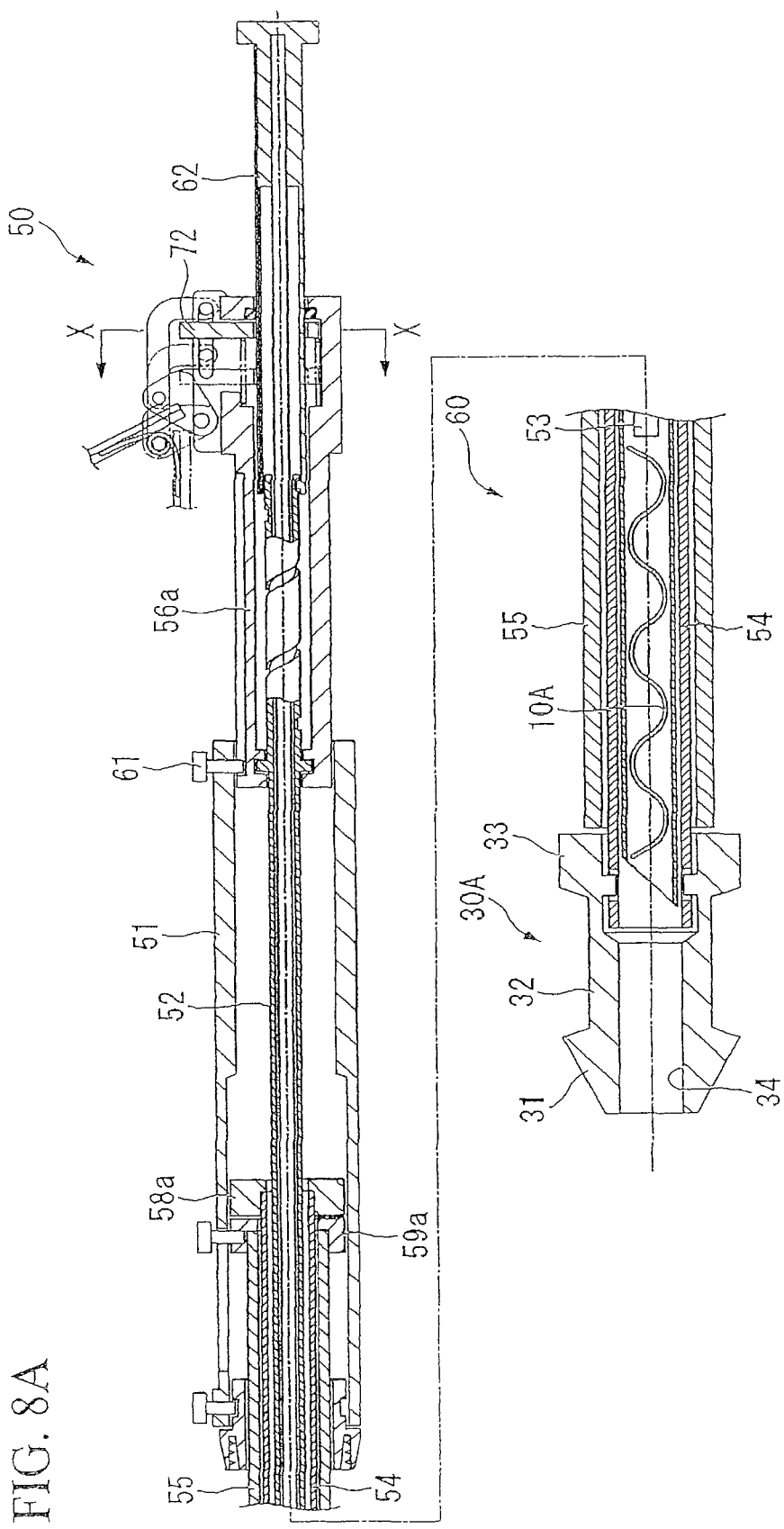
FIGS. 8 to 14 are cross-sectional diagrams showing states of the applicator in use at each step upon performing a bypass procedure between the common bile duct and the duodenum, after fixing the common bile duct to the duodenum.
Figure 8B:
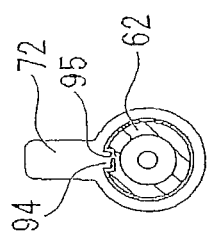

As shown in FIG. 8, prior to a procedure, the applicator 50 is set by retracting the puncturing tool 52 and the stylet 53 relative to the applicator main body 51 by operating the first shaft 56a and the second shaft 62, respectively. Furthermore, the sheath 54 and the stent pusher 55 are also retracted relative to the applicator main body 51 by simultaneous operation of the first ring member 58a and the second ring member 59a, providing that the first ring member 58a should be placed in the vicinity of the second ring member 59a. At this state, the puncturing tool 52 accommodating the tissue fastening tool 10A therein is pulled inside of the sheath 54 until the distal end is positioned in the stent 30A.

The applicator 50 is fixed to the endoscope 2 by inserting the insertion section 60 of the applicator 50 into an instrument channel of the endoscope 2 and advanced, so as to protrude a distal end of the insertion section 60 from a distal end of the insertion section 4 of the endoscope 2. A direction of the protruded insertion portion 60 can be adjusted by the forceps elevator 7.

Figure 9:
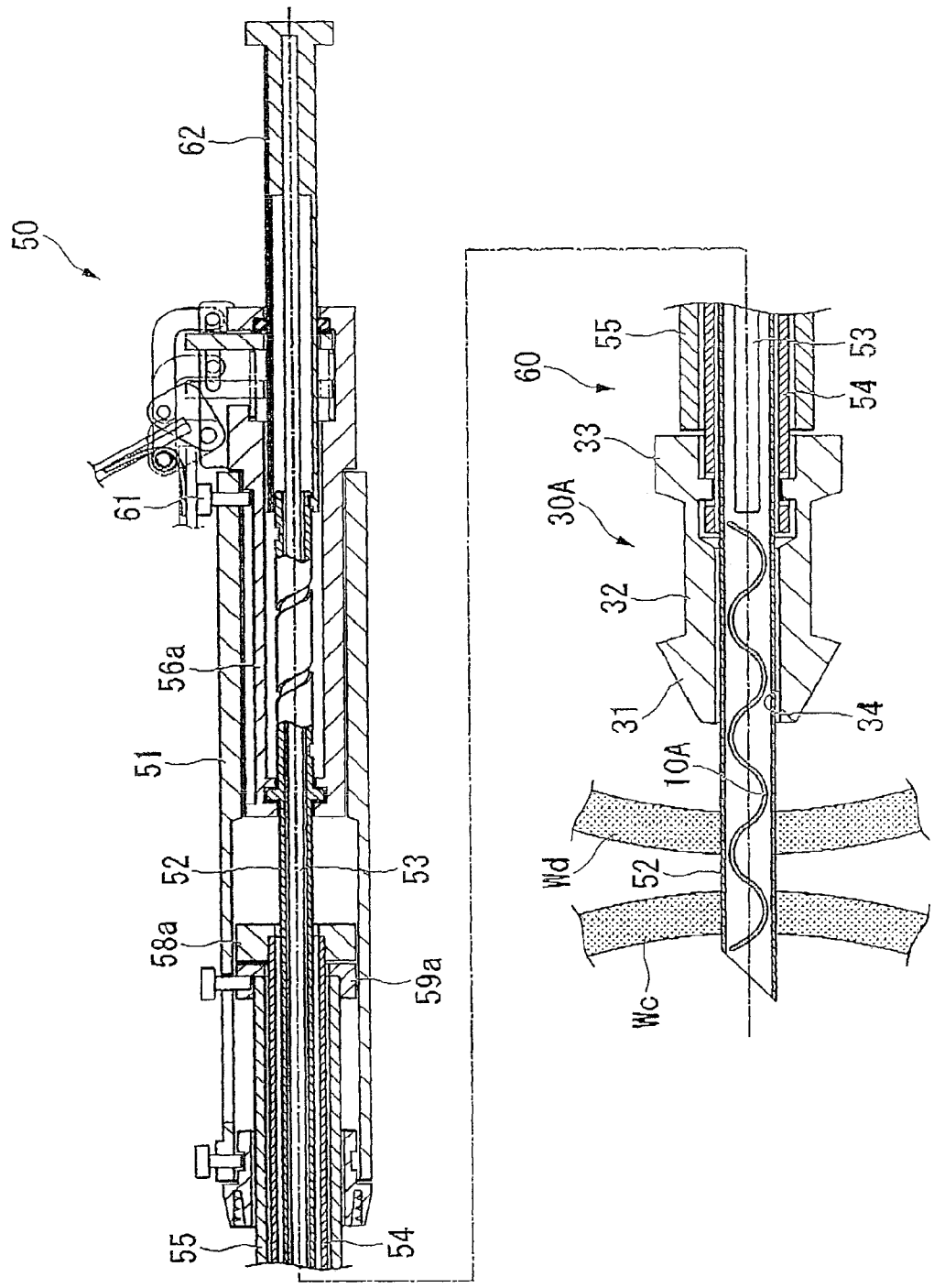

The common bile duct Cb is observed using the ultrasonic probe 6 fitted on the endoscope 2 through the duodenum Dd, and the position in which the puncturing tool 52 will be pierced into the common bile duct Cb is determined. As shown in FIG. 9, the external thread 61 is loosened, the first shaft 56a is pushed into the applicator main body 51, and the distal end of the puncturing tool 52 is made to protrude from the distal end of the stent 30A which is disposed at the distal end of the sheath 54.

As a result, the wall Wd of the duodenum Dd is pierced from the inside. Then, the wall Wc of the common bile duct Cb is pierced from the outside by a sharp distal end of the puncturing tool 52. Then the external thread 61 is tightened so as to fix the first shaft 56a to the applicator main body 51.

Figure 10:
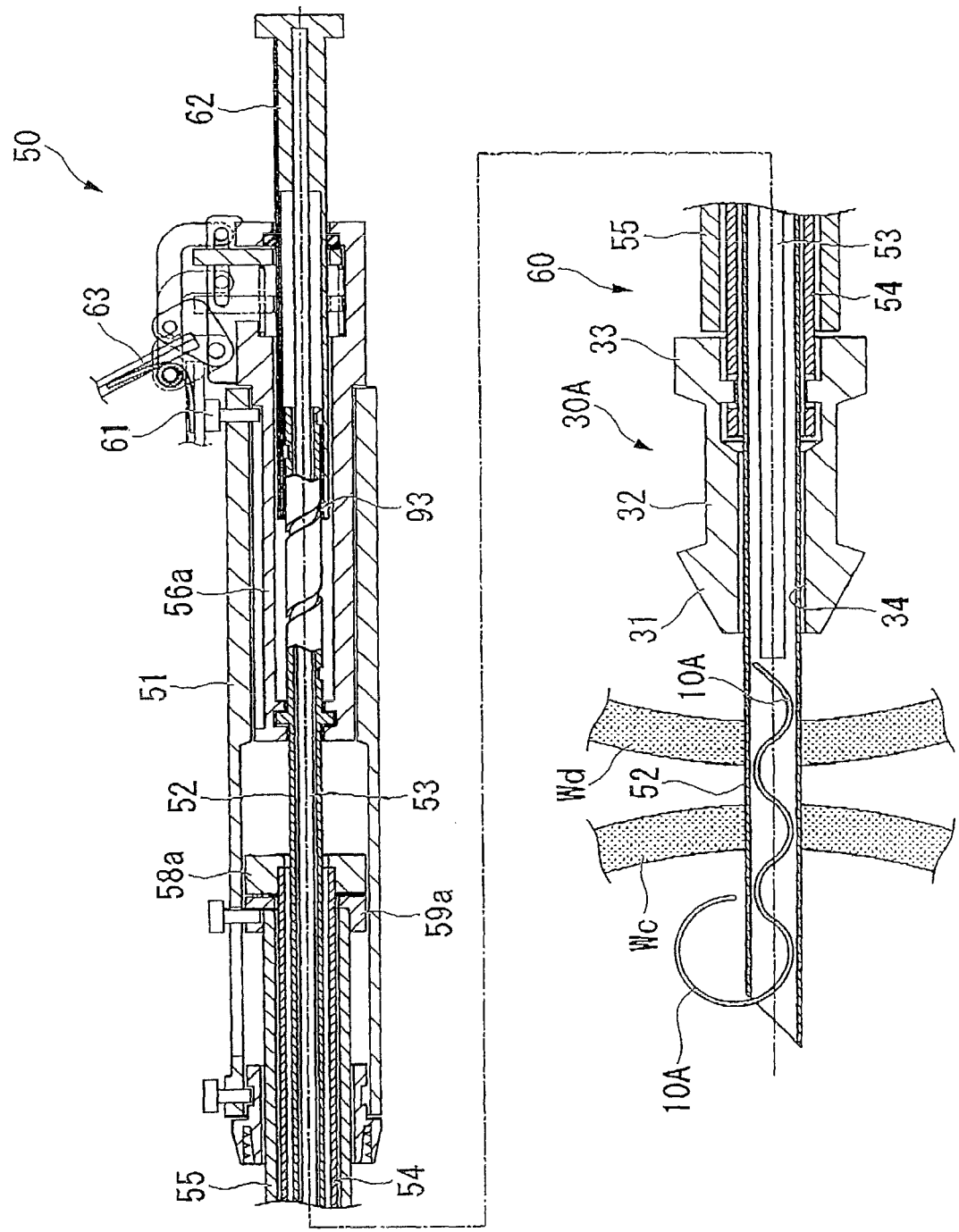

As shown in FIG. 10, the second shaft 62 is pushed into the first shaft 56a by a predetermined amount with operation on the lever 63. For example, when the lever 63 is operated by predetermined times, the stylet 53 changes its relative position to the puncturing tool 52 and the second tissue fixing section 12 of the a tissue fastening tool 10A is pushed out form the distal end of the puncturing tool 52. At this time, the projection 93 formed on the second shaft 62 moves along the spiral groove 92 of the puncturing tool 52 in conjunction with the forward movement of the second shaft 62. On the other hand, the rotation of the second shaft 62 is regulated because of the projection 95 of the plate member 72 engaged with the longitudinal groove 94 formed on the outer periphery of the second shaft 62. As a result, the puncturing tool 52 rotates in conjunction with the forward movement of the second shaft 62. At this time, since the rotation direction of the puncturing tool 52 is set to be opposite with respect to the wounding direction of the tissue fastening tool 10A dispended from the distal end of the puncturing tool 52, the second tissue fixing section 12 dispensed from the puncturing tool is 52 quickly restored to its original coil shape without the shape being distorted (the mechanism will be described later) and hooks onto the inner side of the wall Wc of the common bile duct Cb.

The first shaft 56a is slightly pulled out from the applicator main body 51 by loosening the external thread 61 and the protruded amount of the puncturing tool 52 from the distal end of the stent 30A is reduced.

Then the external thread 61 is tightened so as to fix the first shaft 56a to the applicator main body 51. As a result, the distal end of the puncturing tool 52 is moved slightly away from the internal layer of the wall Wd of the duodenum Dd.

Figure 11:
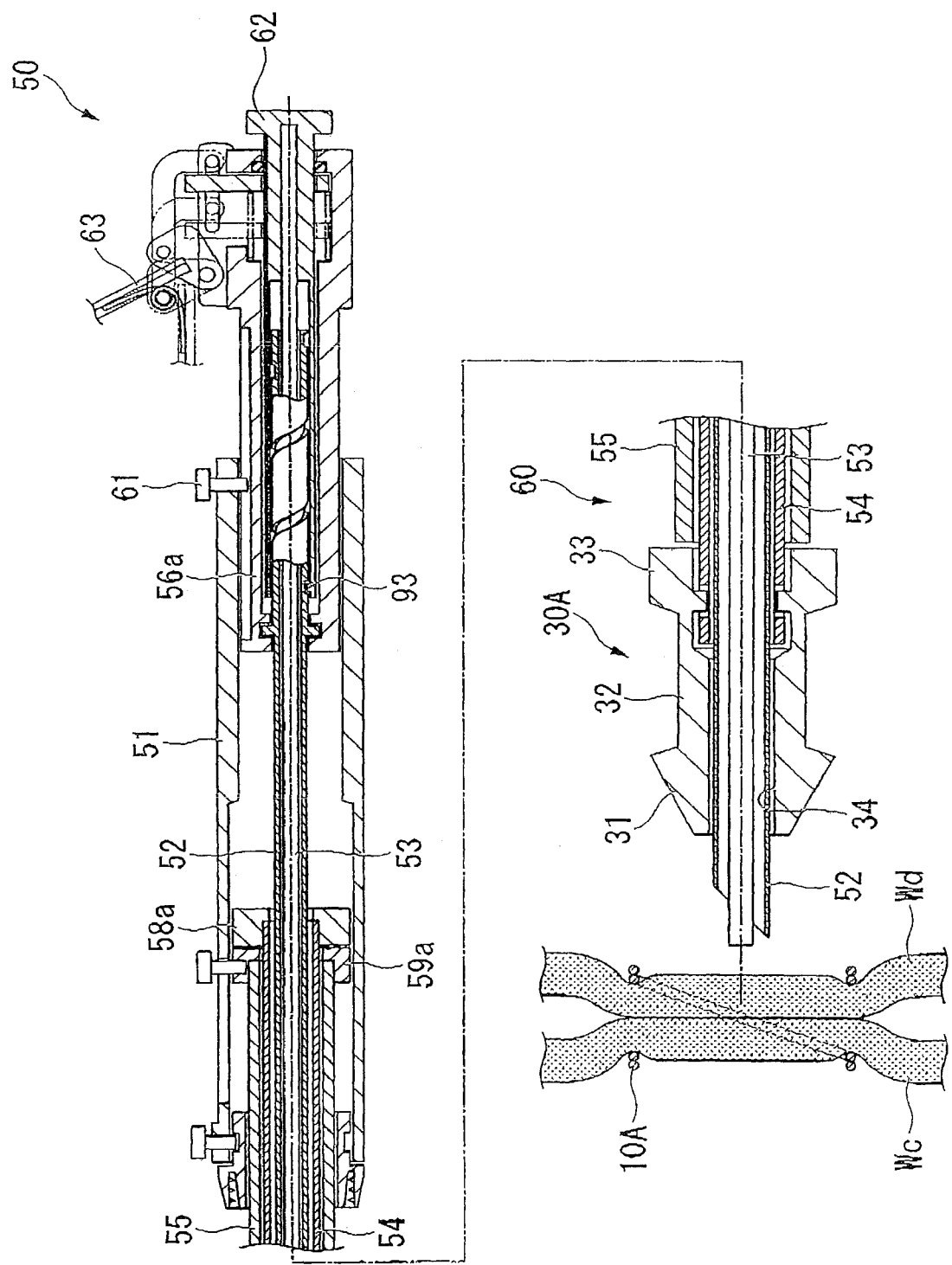

As shown in FIG. 11, the lever 63 is operated again and the second shaft 62 is pushed into the first shaft 56a by a predetermined amount; for example, the lever 63 is operated at predetermined times. As a result, the stylet 53 changes its relative position to the puncturing tool 52 and the connector 13 and the first tissue fixing section 11 of the tissue fastening tool 10A are pushed out form the distal end of the puncturing tool 52. At this time, as described hereinabove, the puncturing tool 52 rotates in the opposite direction of the winding direction of the coil of the tissue fastening tool 10A. As a result, when the first tissue fixing section 11 is dispensed from the puncturing tool 52, the first tissue fixing section 11 is quickly restored to its original coil shape without the shape being distorted (the mechanism will be described later) and hooks onto the inner side of the wall Wd of the duodenum Dd.

When the tissue fastening tool 10A is pushed out from the puncturing tool 52, the coil-shaped tissue fastening tool 10A fastens the duodenum Dd and the common bile duct Cb by clamping the wall Wd of the duodenum Dd hooked by the first tissue fixing section 11 and the wall Wc of the common bile duct Cb hooked by the second tissue fixing section 12.

Figure 12:
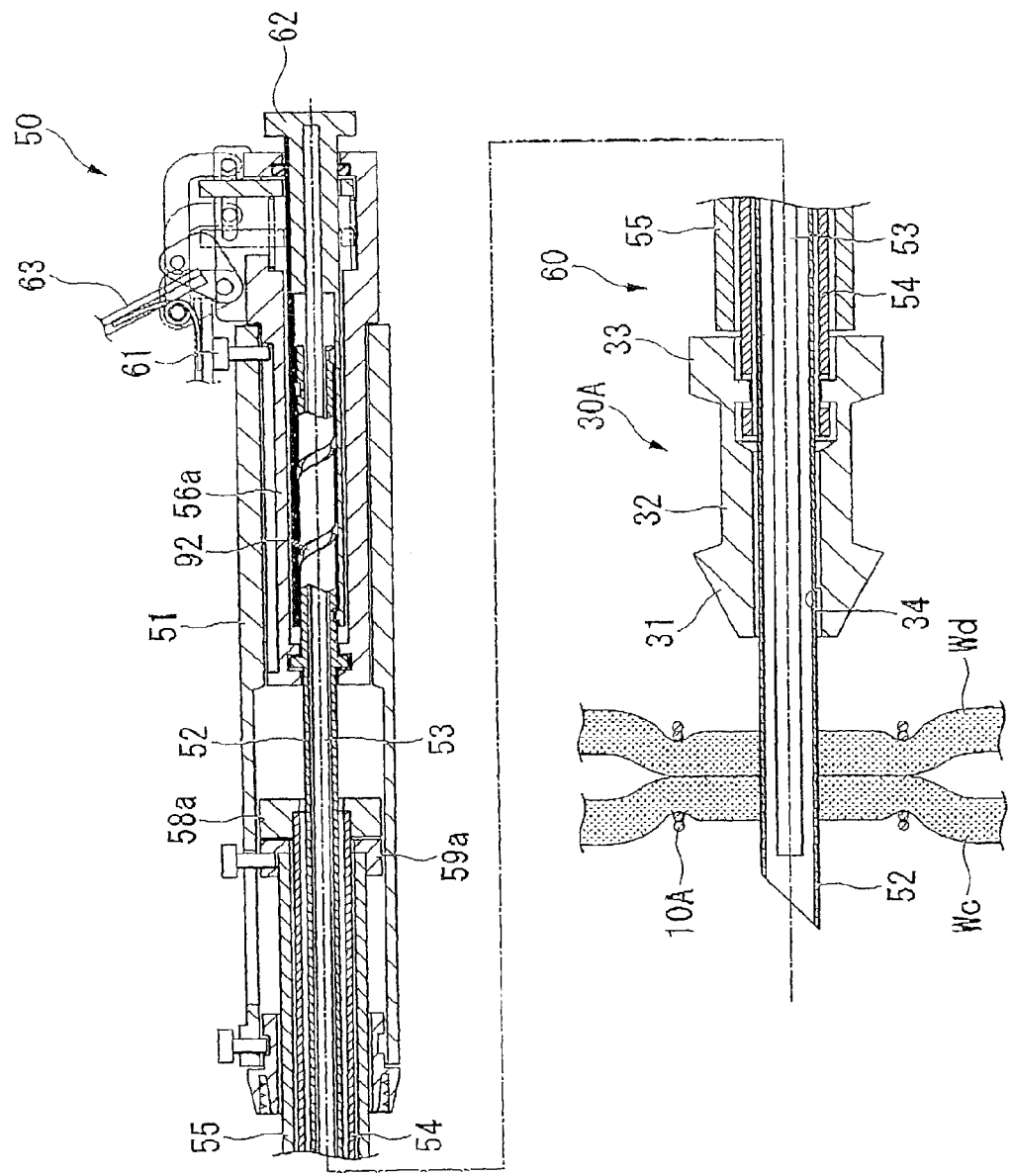

As shown in FIG. 12, the distal end of the stylet 53 is housed inside of the puncturing tool 52 by slightly retracting the second shaft 62. Then the first shaft 56a is advanced into the applicator main body 51 by loosening the external thread 61 and the distal end of the puncturing tool 52 is made to protrude from the distal end of the stent 30A. As a result, the sharp end of the puncturing tool 52 is made to pierce through an area of the wall Wd of the duodenum Dd and the wall Wc of the common bile duct Cb surrounded by the tissue fastening tool 10A. Then the first shaft 56a is fixed to the applicator main body 51 by tightening the external thread 61, and the second shaft 62 is completely pushed into the first shaft 56a by operating the lever 63. By virtue of this mechanism, the smooth distal end of the stylet 53 is protruded from the sharp distal end of the puncturing tool 52; consequently, damage to the peripheral tissues by the sharp distal end of the puncturing tool 52 can be prevented.

Figure 13:
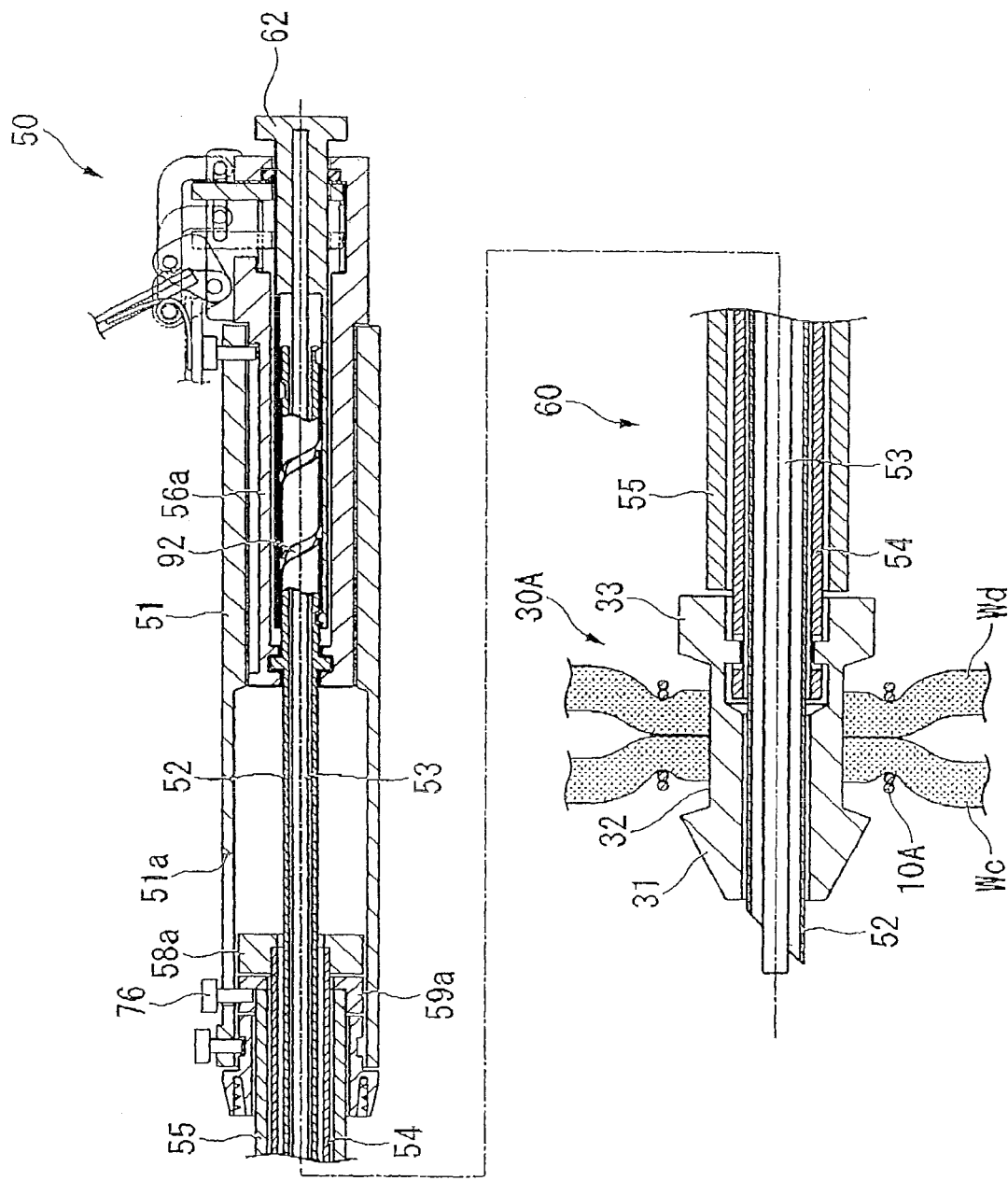

As shown in FIG. 13, the first ring member 58a and the second ring member 59a are advanced toward the distal end of the applicator main body 51 by loosening the external thread 76. By this advancement, the relative positions of the sheath 54 and the stent pusher 55 with the puncturing tool 52 at a fixed state where the first shaft 56a is housed in the applicator main body 51 are changed, consequently the stent 30A is pushed along the puncturing tool 52. The dilating portion 31 of the stent 30A is made to pierce into the area surrounded by the tissue fastening tool 10A where a perforation is created by the puncturing tool 52, from the wall Wd of the duodenum Dd into the wall Wc of the common bile duct Cb so as to widen the perforation by the puncturing tool 52. When the dilating portion 31 penetrates through the wall Wd of the duodenum Dd and the wall Wc of the common bile duct Cb, the stent 30A is indwelled between the wall Wd of the duodenum Dd and the wall Wc of the common bile duct Cb in a state in which the indwelled portion 32 is placed between the wall Wd and the wall Wc. The dilating portion 31 is protruded into the common bile duct Cb and the fall-off prevention portion 33 is placed inside of the duodenum Dd. After the stent 30A is indwelled, the second ring member 59a is fixed to the applicator main body 51 by fastening the external thread 76.

Figure 14:
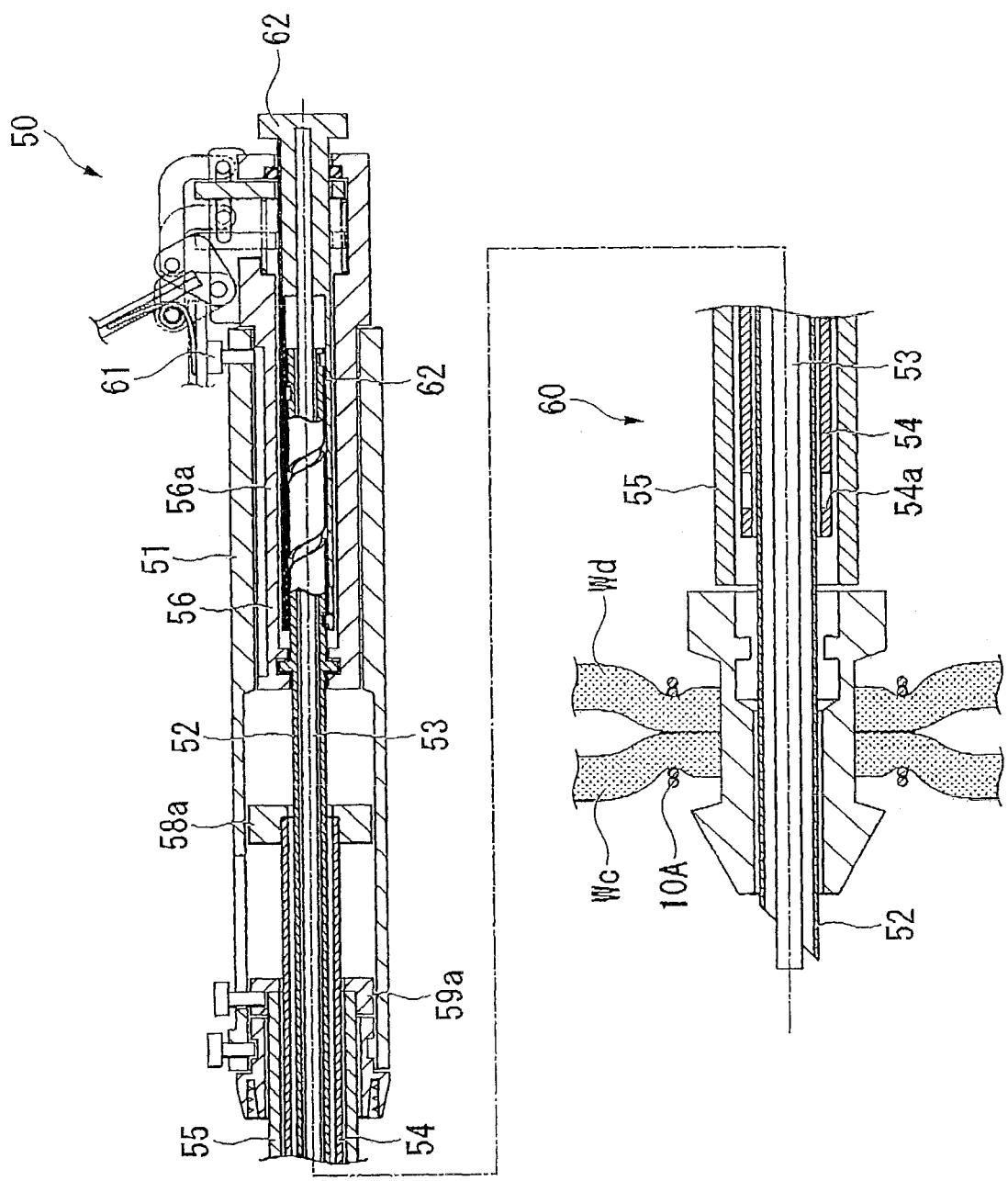

Then the first ring member 58a is retracted toward the rear end of the applicator main body 51 as shown in FIG. 14 by pushing the pin 77 shown in FIG. 4 into the applicator main body 51 At this time, the relative position between the sheath 54 and the stent pusher 55 is changed since the second ring member 59a is fixed to the applicator main body 51 and the sheath 54 is retracted toward the proximal side. However since the stent 30A is in contact with the distal face of the stent pusher 55, a force to resist movement acts on the stent 30A. As a result, the distal end of the sheath 54 is elastically deformed causing a separation of the projections 33a of the stent 30A from the small holes 54a of the sheath 54. When the projections 33a separates from the small holes 54a, the distal end of the sheath 54 is retracted into the stent pusher 55. Consequently, the stent 30A is separated from the distal end of the insertion section 60 of the applicator 50.

The first shaft 56a is retracted from the applicator main body 51 by loosening the external thread 61 and the distal end of the puncturing tool 52 is retracted into the distal end of the sheath 54. Then the first shaft 56a is fixed to the applicator main body 51 by tightening the external thread 61 and the applicator 50 is detached from the endoscope 2. In this manner, the procedures of fastening the wall Wd of the duodenum Dd and the wall Wc of the common bile duct Cb by the tissue fastening tool 10A, and indwelling the stent 30A in the wall Wd of the duodenum Dd and the wall Wc of the common bile duct Cb are completed. By virtue of the above described procedures, the duodenum Dd and the common bile duct Cb are joined through the through hole 34 of the stent 30A, consequently bile flows from the common bile duct Cb into the duodenum Dd.

When the tissue fastening tool 10A is indwelled inside of the body, the wall Wd of the duodenum Dd and the wall Wc of the common bile duct Cb are compressed by the tissue fastening tool 10A, the tissue inside of the area fastened by the tissue fastening tool 10A becomes ischemic condition. When the ischemic condition is prolonged, the tissue within the area fastened by the tissue fastening tool 10A becomes necrotized. On the other hand, the duodenum wall Wd and the common bile duct wall Wc coalesce and join with each other all around at the outer periphery of the tissue fastening tool 10A. When this occurs, the necrotized tissue falls off from the duodenum wall Wd and the common bile duct wall Wc along with the tissue fastening tool 10A and the stent 30A. The tissue fastening tool 10A and the stent 30A are later discharged. An anastomosis hole is formed between the Duodenum wall Wd and the Common bile duct wall Wc after the tissue falls off. The duodenum Dd and the common bile duct ab are joined through the anastomosis hole, hence bile flows from the common bile duct Cb into the duodenum Dd. Since the portion all around the anastomosis hole connecting the duodenum Dd and the common bile duct Cb has coalesced; therefore there is no concern of bile leaking out from between the duodenum wall Wd and the common bile duct wall Wc into the abdominal cavity.

According to the applicator 50 in the present invention, the tissue fastening tool 10A can be pushed out from the puncturing tool 52 easily with high precision by simply operating the lever 63 even with the application of a small force. In addition, the stent 30A can be separated from the distal end of the sheath 54 in a timely manner. For this reason, the tissue fastening tool 10A and the stent 30A can be indwelled at any desired position within the body.

Furthermore, when the stent 30A is pressed against the wall Wd of the duodenum wall Dd and the wall Wc of the common bile duct Cb by using the sheath 54 and the stent pusher 55, the puncturing tool 52 is maintained in its predetermined position so as to prevent unnecessary damage to organs; hence safe operation is ensured.

Next, movement of the tissue fastening tool 10A which is protruded from the distal end of the puncturing tool 52 will be explained.

Firstly, the tissue fastening tool 10A is dispensed such that the second tissue fixing section 12 protrudes from the distal end of the puncturing tool 52 which has penetrated through the wall Wd of the duodenum Dd and the wall Wc of the common bile duct Cb. The second tissue fixing section 12 is hooked onto the wall Wc of the common bile duct Cb by gradually restoring into its original coil shape while being pushed out from the distal end of the puncturing tool 52.

Figure 15A:
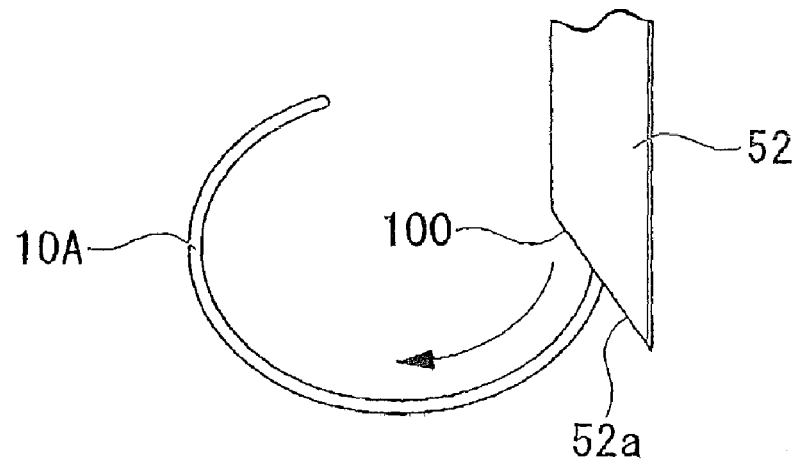
FIGS. 15 to 24 are views showing movements of the tissue fastening tools dispensed from the puncturing tools.
Figure 15B:
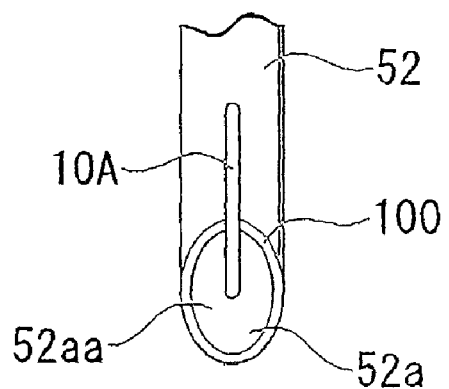

The tissue fastening tool 10A housed in the puncturing tool 52 always tends to curl up in order to be restored to the original shape due to its elastic force. Thus, when the tissue fastening tool 10A is dispensed from the distal end of the puncturing tool 52, it is dispensed while abutting the inner surface side of the fastening tool 10A to an opening 100 which is closest to the base of the shape edge of the puncturing tool 52, as shown in FIGS. 15A and 15B. When the distal end of the puncturing tool 52 has a slant opening 52a slanting like an injection needle, the tissue fastening tool 10A is dispensed from the highest position of the slant opening 52a and tends to restore into the original shape while positioning on a substantially perpendicular surface with respect to a slant opening 52aa.

Thereby, when the puncturing tool 52 is rotated while the tissue fastening tool 10A is being dispensed from the slant opening 52a of the puncturing tool 52, the tissue fastening tool 10A integrally rotates with the puncturing tool 52.

A placing method of the tissue fastening tool 10A using a function of the tissue fastening tool 10A and the puncturing tool 52 which are integrally rotated is explained hereinbelow.

When the tissue fastening tool 10A does not touch the surrounding wall of common bile duct Wc upon dispension of the tissue fastening tool 10A from the puncturing tool 52, the tissue fastening tool 10A restores correctly into its original shape. However, when the tissue fastening tool 10A touches to the surrounding wall of common bile duct Wc, the tissue fastening tool 10A often may not be able to be restored to its original shape.

Figure 16A:
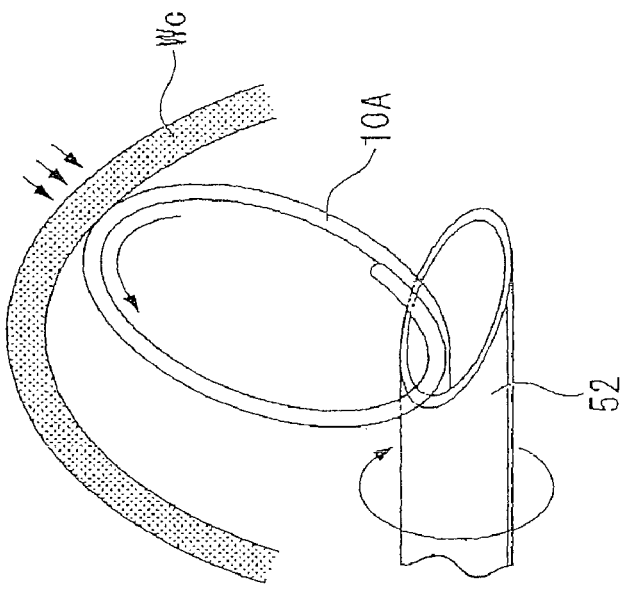
Figure 16B:
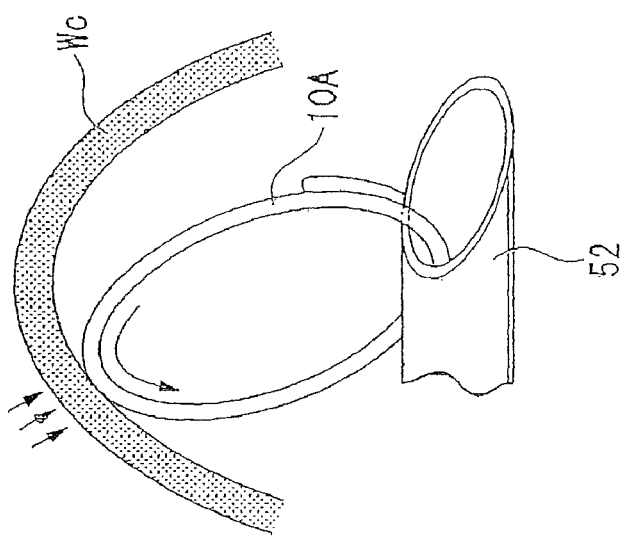

Taking a right-handed coil as an example, the tissue fastening tool 10A is further dispensed from the puncturing tool 52 in the state shown in FIGS. 15A and 15B, the tissue fastening tool 10A is restored to a right-handed coil as shown in FIG. 16A in a normal case. However, if the tissue fastening tool 10A touches to the wall of common bile duct Wc as shown in FIG. 16B, there is a possibility of it being formed into a left-handed coil which has an opposite winding direction from the original shape by being pushed by the wall of common bile duct Wc.

Figure 16C:
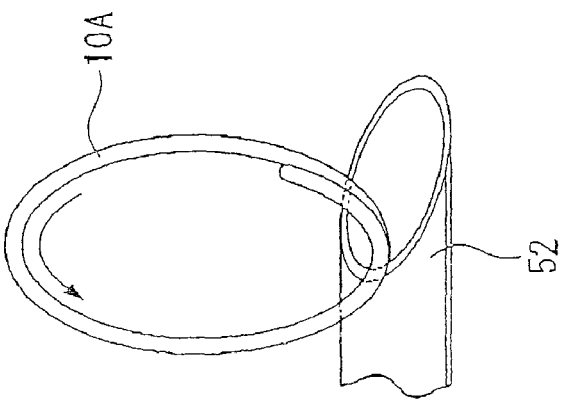

In order to prevent the coil from being wound in the opposite direction, if the tissue fastening tool 10A is a right-handed coil, the puncturing tool 52 is rotated to the left, which is the opposite direction to the winding direction to the tissue fastening tool 10A as shown in FIG. 16C. Then, the tissue fastening tool 10A is dispensed from the puncturing tool 52 by integrally rotating with the puncturing tool 52.

Thereby, the tissue fastening tool 10A rotates left with the puncturing tool 52 so as to push the wall of common bile duct Wc, resulting in restoration of its original shape.

After the second tissue fixing section 12 of the tissue fastening tool 10A is dispensed from the puncturing tool 52 inside of the common bile duct Cb, a remaining tissue fastening tool 10A which includes the first tissue fixing section 11, is completely dispensed from the distal end of the puncturing tool 52 which is extracted from the wall Wd of the duodenum Dd and the wall Wc of the common bile duct Cb. At this time, as described previously, the tissue fastening tool 10A is dispended from the slant opening 52a of the puncturing tool 52 while the puncturing tool 52 is being rotated so as to be able to place the tissue fastening tool 10A smoothly.

Figure 17:
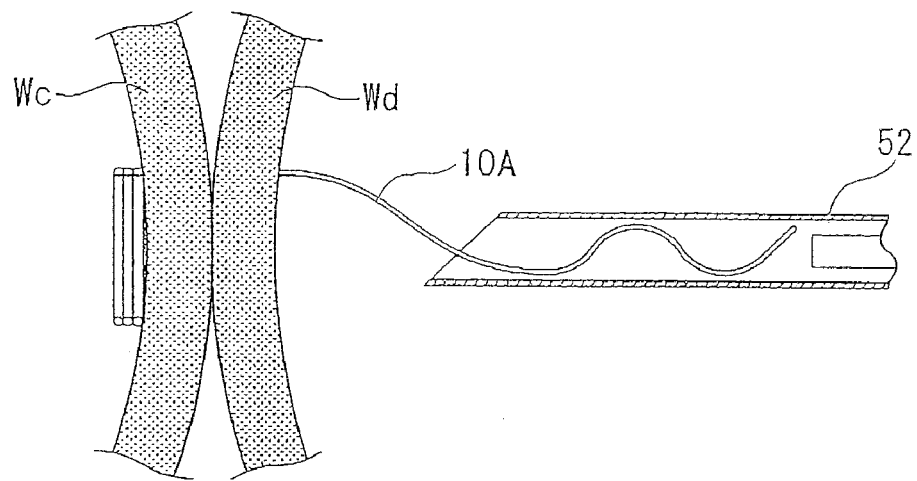
Figure 18:
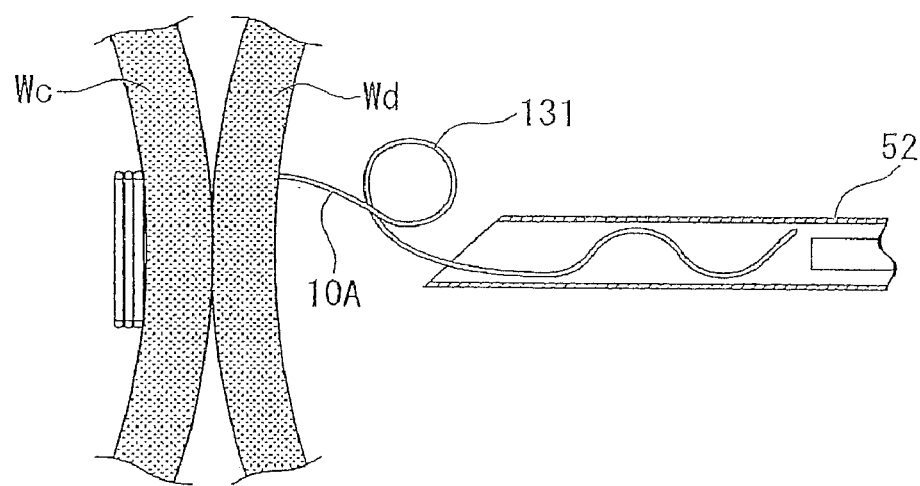
Figure 19:
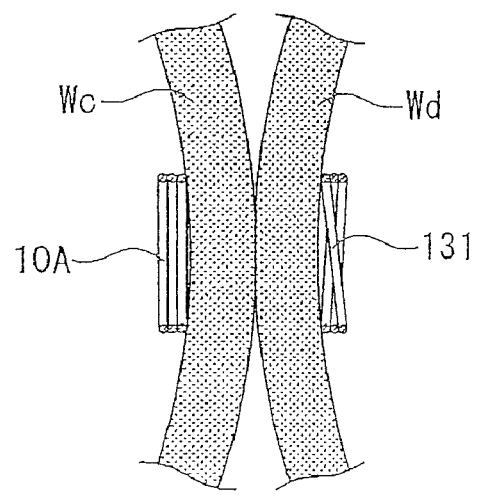
Figure 20:
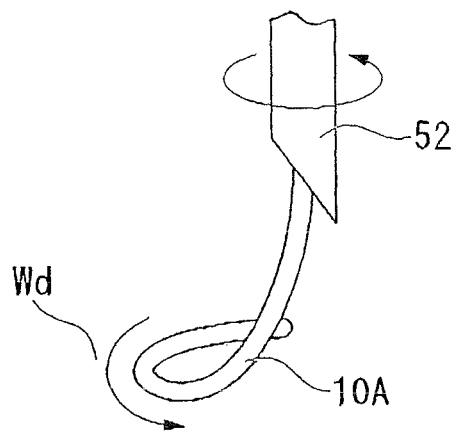
Figure 21:
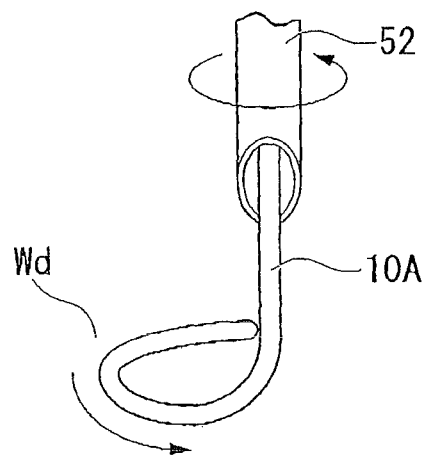
Figure 22:
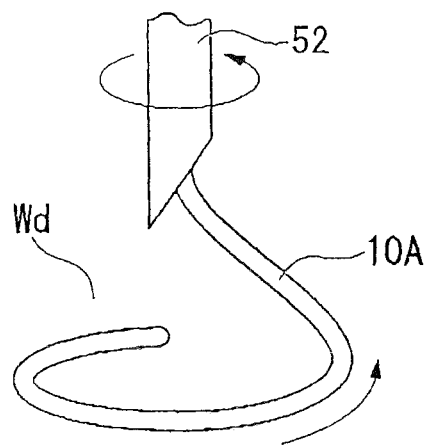
Figure 23:
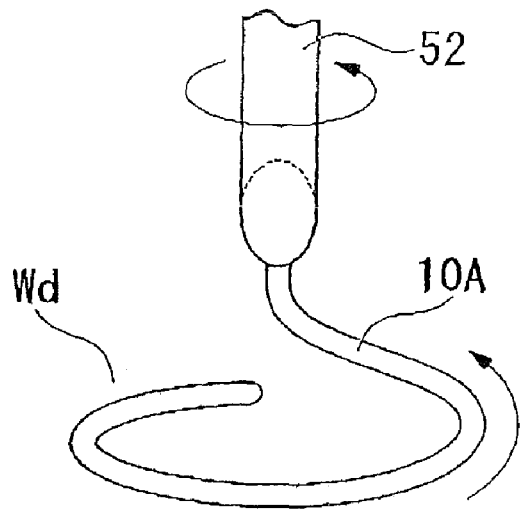
Figure 24:
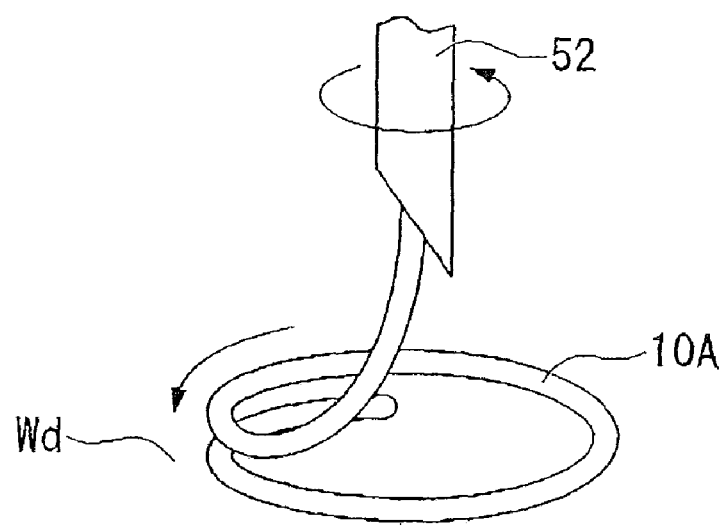

FIGS. 17 to 19 are explanatory views of a problem causing when the tissue fastening tool 10A is hooked onto the first biological tissue after the tissue fastening tool 10A is hooked onto the second biological tissue. As explained in the figures, when the tissue fastening tool 10A is hooked onto the wall Wd of the duodenum Dd as the first biological tissue after the tissue fastening tool 10A is hooked onto the wall Wc of the common bile duct Cb as the second biological tissue, as shown in FIG. 18, a contorted portion 131 occurs due to the original coiling shape restoring force of the tissue fastening tool 10A. As a result, there are possibilities in which the tissue fastening tool 10A may be placed in entangled state as the contorted portion 131 being the staring point for the entanglement, as shown in FIG. 19.

The entanglement problem of the tissue fastening tool 10A at the time of placement can be prevented by integrally rotating the tissue fastening tool 10A and the puncturing tool 52. The mechanism is described hereinbelow.

The restoring movement of the tissue fastening tool 10A into its original coil shape when it is placed on the wall Wd of the duodenum Dd is also a rotary movement of the tissue fastening tool 10A on the wall Wd as shown in FIGS. 20 to 24. Thus, if the movement of the tissue fastening tool 10A and that of the puncturing tool 52 are made to be synchronized, the tissue fastening tool 10A can be smoothly placed. In particular, when the tissue fastening tool 10A is dispensed from the distal end of the puncturing tool 52 by substantially one-coil wind, a coil is set to rotate substantially one round.

Figure 25:
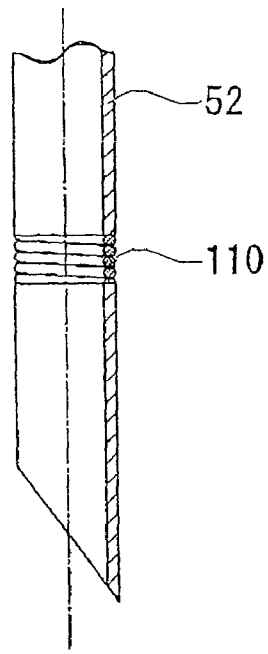
FIGS. 25 to 28 are external views showing modification examples of the distal end of the puncturing tool.
Figure 26:
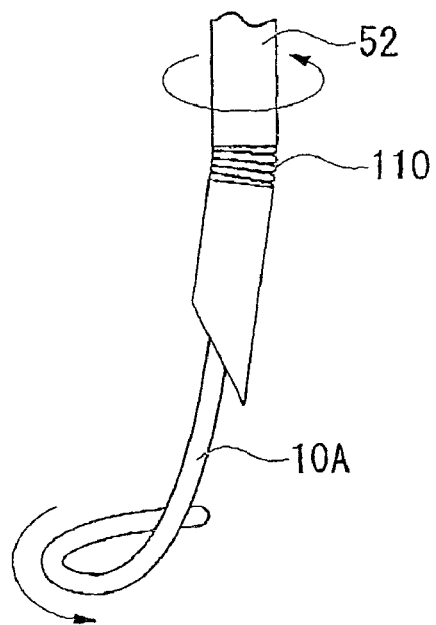

Taking the right-handed coil as an example, as shown in FIGS. 20 to 24, the placement of the tissue fastening tool 10A can be performed smoothly by rotating the puncturing tool 52 in the opposite direction to the wounding direction of the tissue fastening tool 10A; in other words, the puncturing tool 52 is rotated to the left if the tissue fastening tool 10A is a right-handed coil The distal end of the puncturing tool 52 may be designed to move freely by a certain degree. As shown in FIGS. 25 and 26, a coil spring 110 may be disposed in a position slightly proximal side with respect to the distal end of the puncturing tool 52 so that the distal end side of the puncturing tool 52 with respect to the position of the coil spring 110 moves freely. In this way, the distal end of the puncturing tool 52 may be freely oscillated by following the movement of the tissue fastening tool 10A. Thereby, the tissue fastening tool 10A can be more smoothly placed.

When the first tissue fixing section 11 and the second tissue fixing section 12 of the tissue fastening tool 10A are dispensed from the puncturing tool 52, it is preferable to integrally rotate the tissue fastening tool 10A and the puncturing tool 52, and for the for winding direction of the fastening tool 10A and the rotary direction of the puncturing tool 52 to be opposite.

The first tissue fixing section 11 is hooked onto the wall Wd of the duodenum Dd by gradually returning to its original coil shape while being pushed out from the distal end of the puncturing tool 52.

By hooking the first tissue fixing section 11 and the second tissue fixing section 12 onto the wall Wd of the duodenum Dd and the wall Wc of the Common bile duct. Cd, respectively, then the wall Wd and the wall Wc are fastened. The connector 13 is placed within the fastened duodenum wall Wd and the common bile duct wall Wc. A gap G is provided between the first tissue fixing section 11 and the second tissue fixing section 12 so as to fasten the duodenum wall Wd and common bile duct wall Wc such that they are pressed against each other with equal force.

Here, an angle $\theta 1$ formed between the first tissue fixing section 11 and the connector 13 and an angle $\theta 2$ formed between the second tissue fixing section 12 and the connector 13 are preferred to be less than or equal to 45 degrees (refer to FIG. 3). If the angles $\theta 1$ and $\theta 2$ are greater than 45 degrees, a strong friction force will be generated upon dispensing the tissue fastening tool 10A from the distal end of the puncturing tool 52 because at lease one of the bending section 14 forming the angle $\theta 1$ and the bending section 15 forming the angle $\theta 2$ will come into contact with the inside of the puncturing tool 52. Consequently, it will be difficult to smoothly dispense the tissue fastening tool 10A from the puncturing tool 52.

The size of the gap G between the first tissue fixing section 11 and the second tissue fixing section 12 may preferably be less than or equal to 15 mm. If the size of the gap G is less than or equal to 15 mm, biological tissues of almost all organs accessible by the endoscope 2 can be fixed with the applicator 50.

A plurality of types of the tissue fastening tools 10A with various sizes of the gaps G are provided in order to suit various thicknesses of target organs and characteristics of individual patients. By selecting suitable tissue fastening tools, suitable treatments can be performed for different conditions.

Figure 27:
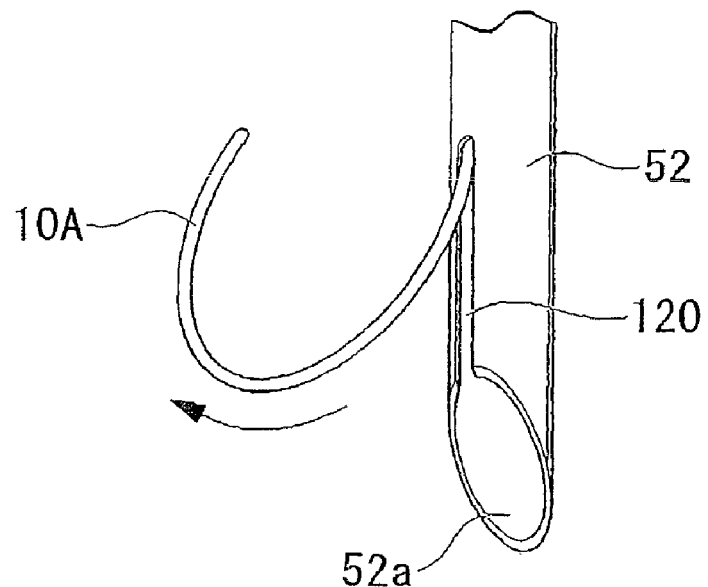

The design of the puncturing tool 52 is not limited to the sharp edge having the slant opening 52a at the distal end as shown in FIGS. 15 and 17 which are similar to an injection needle. It is also acceptable to have the slant opening 52a and is further provided with a slit 120 extending from the proximal side to the distal end along an axial direction, as shown in FIG. 27.

Figure 28:
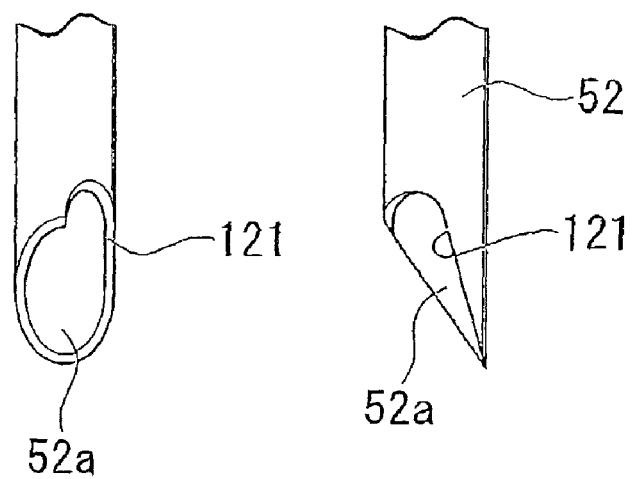

Furthermore, as shown in FIG. 28, the distal end of the puncturing tool 52 may be provided with the slant opening 52a at the distal end and farther provided with a cut out portion 121 which is cut out widely from a center of the proximal side into one of the side of the distal end.

Thereby, by farther providing the slit 120 and the cut out portion 121 on the premise of providing the slant opening 52a, the tissue fastening tool 10A can be fixed to the slit 120 and the cut out portion 121. As a result, when the puncturing tool 52 is rotated, the tissue fastening tools 10A can be rotated integrally therewith, the tissue fastening tools 10A can be smoothly placed without causing the tissue fastening tools 10A to be oppositely winded.

In addition, it is not necessary for the slit 120 and the cut out portion 121 to be provided on the premise of providing the slant opening 52a; the slit 120 and the cut out portion 121 may also be provided on a horizontal opening.

In order to avoid the entanglement of the tissue fastening tools 10A at the time of placement, apart from integrally rotating the tissue fastening tools 10A and the puncturing tool 52, it is more effective to increase the rigidity of a connecting portion between the first tissue fixing section 11 hooked onto the first biological tissue and the second tissue fixing section 12 hooked onto the second biological tissue.

Figure 29:
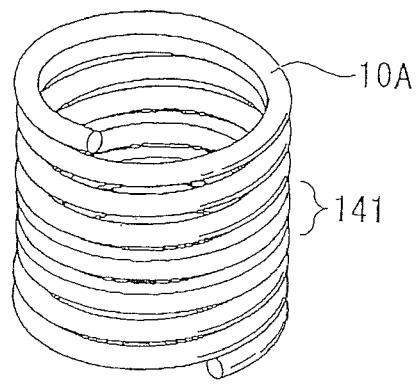
FIGS. 29 to 33 are external views showing modification examples of tissue fastening tools.
Figure 30:
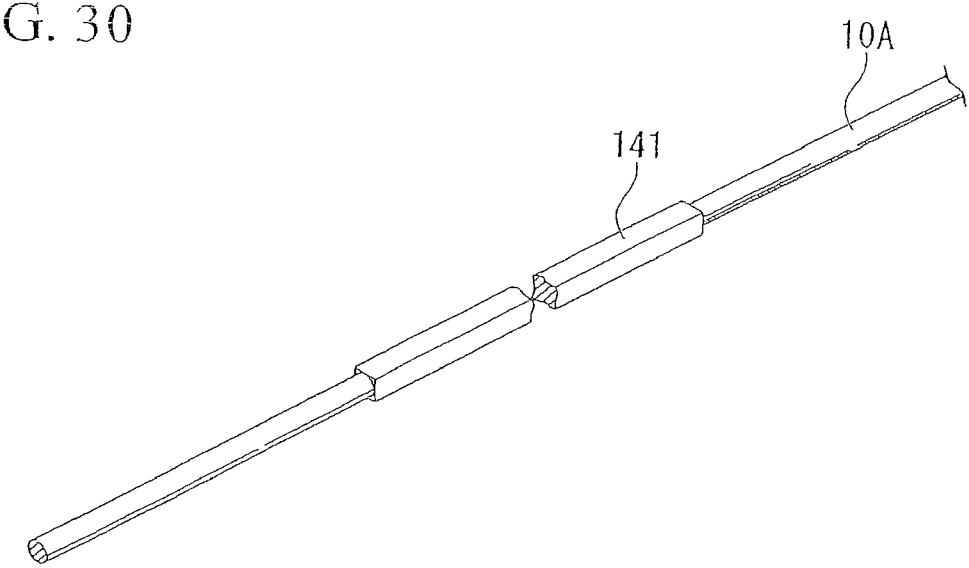

For example, as shown in FIG. 29, it is also acceptable to design cross sections of the first tissue fixing section 11 and the second tissue fixing section 12 to be a circular shape, and only the design of a cross section of the connecting portion 141 to be a rectangular shape. In virtue of the design being the rectangular shape, a spring constant of the connecting portion 141 can be set higher than that of other circular cross section. Furthermore, as soon as the first tissue fixing section 11 is hooked onto the first biological tissue begins to be dispensed, the tissue fastening tools 10A tend to return to its original coil shape; however, the occurrence of entanglement at some distance apart from the first biological tissue, such as the wall Wd of the duodenum Dd, as shown in FIG. 18, can be prevented. In addition, by having the rectangular cross section, the spring has an advantage of easily returning to its original shape after it is stretched.

Figure 31:
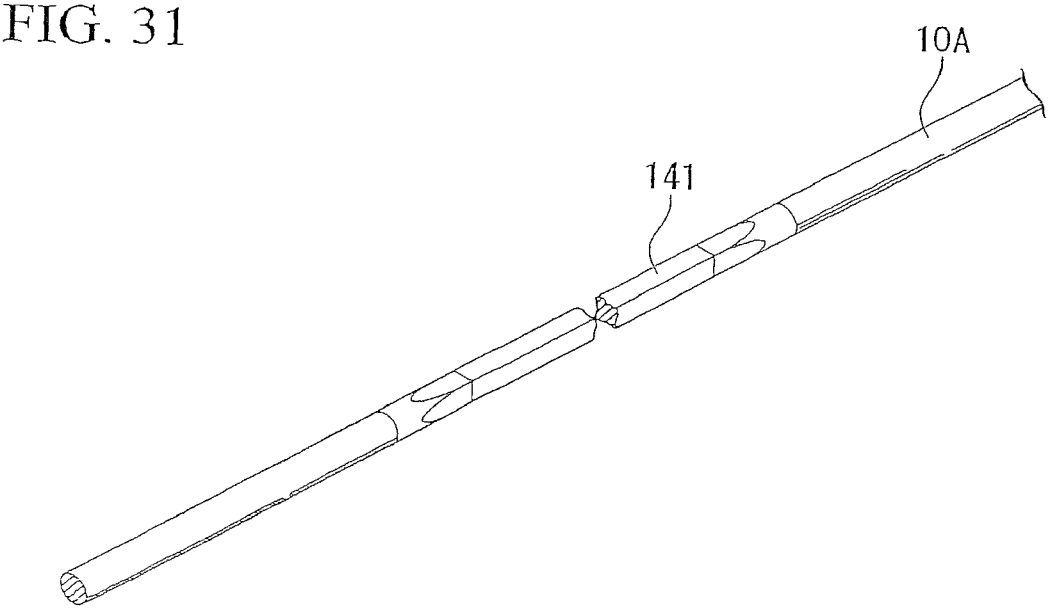

When forming the rectangular cross section of the connecting portion 141 between the first tissue fixing section 11 and the second tissue fixing section 12, the rectangular cross section may be formed by removing arc portions of the circular cross section so that the rectangular cross section becomes thinner as shown in FIG. 31; however, the rectangular cross section may also be formed to be thicker than the circular cross section as shown in FIG. 31.

Figure 32:
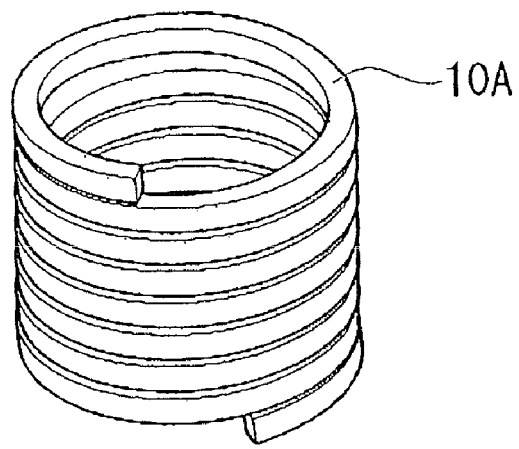
Figure 33:
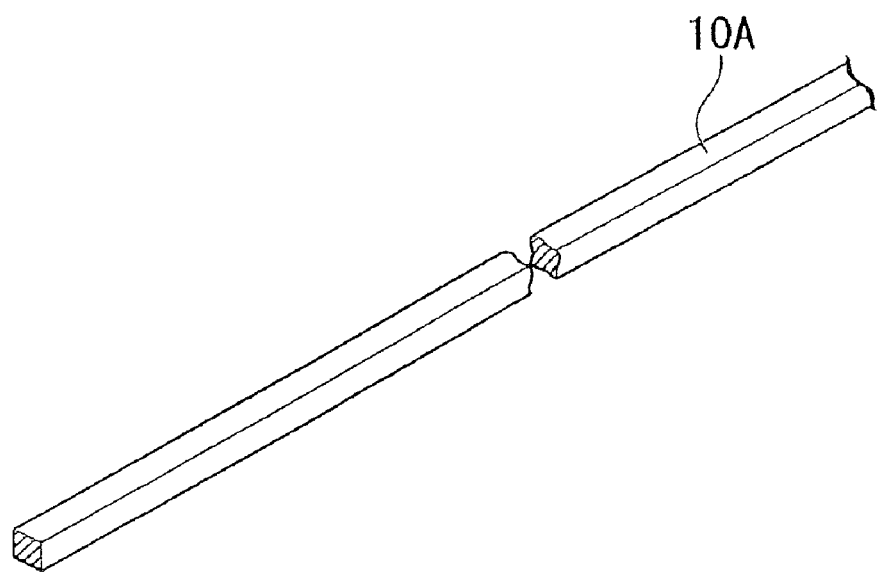

Furthermore, it is also acceptable to not only form the rectangular cross section at the connecting portion 141 between the first tissue fixing section 11 and the second tissue fixing section 12, but also to form the rectangular cross section to the entire tissue fastening tools 10A including the connecting portion 141, such as shown in FIGS. 32 and 33. Having the rectangular cross section, the coil has more resistance to getting entangled compared to that of the circular cross section, hence the occurrence of entanglement at the beginning of dispension of the first tissue fixing section 11 hooked onto the first biological tissue can be prevented. In addition, the cross section of the connecting portion or/and the entire tissue fastening tools 10A may also formed to be polygonal shape.

Second Embodiment

The second embodiment of the present invention will be explained referring to FIG. 34. In the following description, components that are the same as the first embodiment shall be provided with the same numeric symbol and redundant descriptions shall be omitted.

Figure 34:
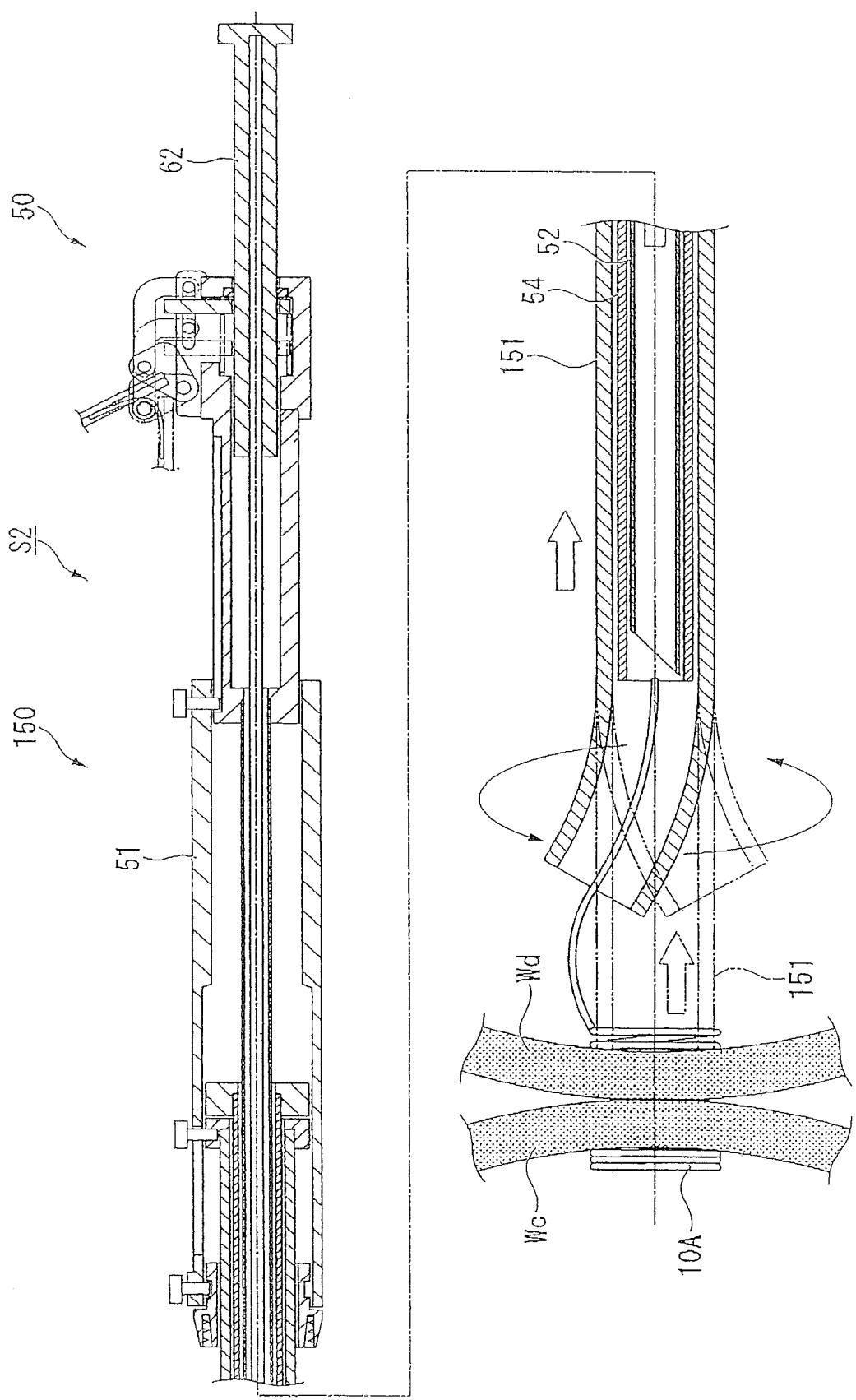
FIG. 34 shows a tissue fastening apparatus in the second embodiment of the present invention and is a cross-sectional view showing the internal structures of a tissue fastening tool, a stent and an applicator included in the apparatus.

A tissue fastening apparatus S2 of the present embodiment includes the tissue fastening tool 10A, and an applicator 150 as shown in FIG. 34. The applicator 150 is not provided with a rotating mechanism to rotate the puncturing tool 52 when the second shaft 62 and the stylet advance. Instead, the applicator 150 is provided with a moving portion at the distal end of the puncturing tool 52 or further front portion thereof, which follows a winding movement when it is dispensed from the distal end of the puncturing tool 52 due to a core set of the tissue fastening tool 10A.

A flexible tube 151 consists of a moving portion disposed on an outer surface of the sleeve 54 and the distal end of the flexible tube can extend forward farther than the distal end of the puncturing tool 52.

In this embodiment, the distal end of the flexible tube 151 extends forward further than the distal end of the puncturing tool 52 so as to abut the first biological tissue, such as the wall Wd of the duodenum Dd. In this state, the second tissue fixing section 12 of the tissue fastening tool 10A is dispensed from the distal end of the puncturing tool 52 and moves due to its elastic force of returning to its original shape. Thereby, the shape of the flexible tube 151 is deformed following the movement of the tissue fastening tool 10A.

Thereafter, the flexible tube 151 is further retracted toward the proximal side, the distal end of the elastic tube gyrates backward due to the force received from the tissue fastening tool 10A as shown in FIG. 34. As described above, the elastic force of the tissue fastening tool 10A is not released at once when it is dispended from the distal end of the puncturing tool 52, the elastic force is controlled by the gyrating distal end of the flexible tube 151 so as to be gradually released. Hence, the tissue fastening tool 10A immediately returns to its original shape without generating the entanglement such as shown in FIG. 18.

Note that the stent 30A is omitted in this embodiment. It is not necessary to place the stent 30A to the biological tissues surrounded by the tissue fastening tool 10A at all the time after the tissue fastening tool 10A is placed; it is also acceptable to incise and create a hole by a high frequency forceps at a center of the biological tissue where the tissue fastening tool 10A is set so as to introduce a bile into a duodenum side.

What is claimed:

1. An applicator comprising:
an elongated member which has an opening at the distal end thereof and includes a lumen including a longitudinal axis, the opening being communicated with the lumen, and the elongated member being configured to extend a tissue fastening tool wound into a coil shape and to have the stretched tissue fastening tool in the lumen;
a pusher which is provided in the lumen configured to be capable of moving in the direction of the longitudinal axis so as to dispense the tissue fastening tool in the lumen from the opening;
an operating section which is provided on a proximal end of the pusher to move the pusher in the direction of the longitudinal axis; and
a rotating mechanism which rotates the elongated member around the longitudinal axis relative to the pusher, as a function of movement of the pusher in the direction of the longitudinal axis relative to the elongated member by operation of the operating section so as to dispense the tissue fastening tool from the opening.

2. The applicator according to claim 1, wherein:
the rotating mechanism is provided with a spiral groove disposed on one of the elongated member and the pusher which engage with each other; and
a projection disposed on the elongated member or the pusher in which the spiral groove is not disposed so as to engage with the spiral groove.

3. The applicator according to claim 1, wherein:
the rotating mechanism is provided with a spiral convex disposed on one of the elongated member and the pusher which engage with each other; and
a projection disposed on the elongated member or the pusher in which the spiral convex is not disposed so as to engage with the spiral convex.

4. The applicator according to claim 1, wherein:
in the rotating mechanism, the amount of the tissue fastening tool dispensed by the pusher and the rotation angle when the elongated member rotates are related.

5. The applicator according to claim 4, wherein:
the elongated member rotates substantially one revolution when the tissue fastening tool is dispensed by substantially one winding.

6. The applicator according to claim 1, wherein:
a winding direction of the tissue fastening tool and the rotation direction of the elongated member are related.

7. The applicator according to claim 6, wherein:
the winding direction of the tissue fastening tool and the rotation direction of the elongated member are opposite.

8. The applicator according to claim 1, further comprising:
a rotation regulating portion provided on the distal end of the elongated member which regulates rotary movement of the tissue fastening tool dispensed from the opening, wherein the rotary movement of the tissue fastening tool is around the longitudinal axis of the elongated member.

9. The applicator according to claim 8, wherein:
the rotation regulating portion is a slant opening formed on the distal end of the elongated member.

10. The applicator according to claim 9, wherein:
a slit is formed on the slant opening in which a portion of the tissue fastening tool fixes thereto.

11. The applicator according to claim 1, wherein:
the elongated member is a tubular puncturing tool, and the puncturing tool accommodates the stretched tissue fastening tool therein.

* * * * *